US008454954B2

(12) United States Patent
Schlossmacher et al.

(10) Patent No.: US 8,454,954 B2
(45) Date of Patent: Jun. 4, 2013

(54) TREATMENT OF SYNUCLEINOPATHIES

(75) Inventors: Michael Schlossmacher, Ottawa (CA); Valerie Cullen, Quincy, MA (US); Lamya Shihabuddin, Brighton, MA (US); Seng H. Cheng, Natick, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 321 days.

(21) Appl. No.: 12/600,141

(22) PCT Filed: May 16, 2008

(86) PCT No.: PCT/US2008/064017
§ 371 (c)(1),
(2), (4) Date: Oct. 12, 2010

(87) PCT Pub. No.: WO2008/144591
PCT Pub. Date: Nov. 27, 2008

(65) Prior Publication Data
US 2011/0038851 A1    Feb. 17, 2011

Related U.S. Application Data

(60) Provisional application No. 60/930,462, filed on May 16, 2007, provisional application No. 60/929,554, filed on Jul. 3, 2007.

(51) Int. Cl.
*A61K 38/47*    (2006.01)
(52) U.S. Cl.
USPC ..................................................... 424/130.1
(58) Field of Classification Search
None
See application file for complete search history.

(56) References Cited

U.S. PATENT DOCUMENTS 6,590,074 B1 *    7/2003    O'Brien et al. .............. 530/350
2006/0287358 A1    12/2006    Wustman
2007/0037826 A1    2/2007    Evenou et al.

FOREIGN PATENT DOCUMENTS
WO    WO 2006/133446    12/2006

OTHER PUBLICATIONS

Borlongan et al. (Brain Research. 2002; 956: 211-220).*
Webb et al. (Journal of Biological Chemistry. 2003; 278(27): 25009-25013).*
Roeber et al. (Acta Crystallogr D Biol Crystallogr. Feb. 2003;59(Pt 2):343-4. Epub Jan. 23, 2003).*
Campbell et al. (Orphanet Journal of Rare Diseases 2012; 7(12): 1-7).*
Lwin et al. (Molecular Genetics and Metabolism. 2004: 81: 70-73).*
Cullen et al, "Inter-relationship between glucocerebrosidase expression and alpha-synuclein dynamics in neural cells," Oasis, on-line Abstract submission and invitation system, (presented on Oct. 16, 2006).
Cullen et al., "Physiological release of a-synuclein from neural cells," Society for Neuroscience 2005 Abstract, (presented on Nov. 13, 2005).
Gai et al., "LRRKS in neural inclusions in Parkinson's, Alzheimer's, and related diseases," Society for Neuroscience 2005 Abstract, (presented on Nov. 16, 2005).
International Search Report and Written Opinion for PCT/US2008/064017, mailed Sep. 18, 2008.
International Preliminary Report on Patentability for PCT/US2008/064017, mailed Dec. 3, 2009.
Periquet et al, "Agregated α-Synuclein Mediates Dopaminergic Neurotoxicity In Vivo," The Journal of Neuroscience, 27(12);3338-3346 (2007).
Schlossmacher et al., "Quantification of blood A-synuclein as biomarker candidate for Parkinson's disease," Society for Neuroscience 2005 Abstract, (presented on Nov. 12, 2005).
Sun et al., "Saposin C is Required for Normal Resistance of Acid β-Glucosidase to Proteolytic Degradation," J. Biol. Chem., 278:31918-31923 (2003).
Office Action in Chinese Patent Application No. 200880025136.0; mailed Aug. 31, 2011; 14 pages (with English translation).
Australian Office Action; Application No. 2008254774; mailed Oct. 22, 2012; Applicant: The Brigham and Women's Hospital, Inc.; 4 pages.
Cao Lei, "Treatment Progress of Neurologic Disease Gene," Chemistry of Life vol. 14, No. 4, pp. 27-29, 1994.
Chinese Office Action; Application No. 200880025136.0; issued Jul. 9, 2012; Applicant: The Brigham and Women's Hospital, Inc.; 9 pages.
Chinese Office Action; Application No. 200880025136.0; issued Nov. 15, 2012; Applicant: The Brigham and Women's Hospital, Inc.; 13 pages.
Chunyu; "Mitochondrial DNA and Heart Diseases," Chemistry of Life vol. 14, Issue 4, pp. 29-30, 1994.
European Search Report; Application No. 08755799.7-1223 / 2154969; mailed Jun. 29, 2012; Applicant: The Brigham and Women's Hospital, Inc.; 11 pages.
Goker-Alpan et al., "Glucocerebrosidase Mutation are an Important Risk Factor for Lewy Body Disorders," Neurology, 67:908-910, 2006.
Japanese Office Action; Application No. 2010-508624; issued Nov. 12, 2012; Applicant: The Brigham and Women's Hospital, Inc.; 7 pages.
Jin et al., "Research Progress of Gaucher Disease," Foreign Medical Science Section of Pediatrics vol. 29, No. 5, pp. 274-276, 2002.
Lo Bianco et al., "Lentiviral Vector Delivery of Parkin Prevents Dopaminergic Degeneration in an α-Synuclein Rat Model of Parkinson's Disease," Proc Natl Acad Sci USA. 101:17510-17515; 2004.
Masliah et al., "Effects of Alpha-Synuclein Immunization in a Mouse Model of Parkinson's Disease," Neuron 46:857-868, 2005.
Qi et al., "Functional Organization of Saposin C," J Biol Chem 271:6874-6880, 1996.

(Continued)

*Primary Examiner* — Scott Long
(74) *Attorney, Agent, or Firm* — Fish & Richardson P.C.

(57) ABSTRACT

This invention relates generally to treating synucleinopathies in subjects that are not clinically diagnosed with a lysosomal storage disease, as well as associated methods of making medicaments and screening methods.

11 Claims, 7 Drawing Sheets

OTHER PUBLICATIONS

Roeber et al., "Crystallization and Prelimianry X-ray Analysis of Recombinant Human Acid Beta-Glucocerebrosidase, A Treatment for Gaucher's Disease," Biological Crystallography vol. D59; pp. 343-344; 2003.

Supplementary European Search Report; Application No. 08755799.7-1223 / 2154969; mailed Jul. 17, 2012; Applicant: The Brigham and Women's Hospital, Inc.; 1 page.

* cited by examiner

TREATMENT OF SYNUCLEINOPATHIES

This application claims the benefit of International Application Number PCT/US2008/064017, filed on May 16, 2008, U.S. Provisional Application No. 60/930,462, filed on May 16, 2007, and U.S. Provisional Application No. 60/929,554, filed on Jul. 3, 2007, all of which are incorporated herein by reference in their entirety.

TECHNICAL FIELD

This invention relates generally to treating synucleinopathies that are not lysosomal storage diseases in subjects, as well as associated screening methods.

BACKGROUND

Genetic, neuropathological, and biochemical evidence has implicated an increased steady-state abundance as well as aberrant processing of α-synuclein (αS) in the development of several neurodegenerative disorders including Parkinson disease (PD), dementia with Lewy bodies (DLB), and others (Dawson et al., (2003) Science 302, 819-22; Vila et al., (2004) Nat. Med., 10 Suppl: S58-62).

Genetic evidence demonstrates that point mutations in the α-synuclein-encoding gene are linked to a severe, dominantly-inherited form of PD with early onset (Krueger et al., (1997) Nat. Genet., 18, 106-108; Zarranz et al., (2004) Ann. Neurol., 55(2):164-73; Polymeropoulos et al., (1997) Science, 276:2045-7), implying a "toxic-gain-of-function" pathogenesis. These mutations cause the following amino acid changes: alanine 30→proline (A30P), glutamine 46→lysine (E46K), and alanine 53→threonine (A53T). Furthermore, duplication and triplication of the α-synuclein encoding synuclein, alpha (non A4 component of amyloid precursor) gene (SNCA) have been linked to familial parkinsonism with a combined PD/DLB phenotype, which demonstrates that increased expression rates of even the wild-type (wt) gene can cause disease (Chartier-Harlin et al., (2004) Lancet, 364, 1167-9; Singleton et al., (2003) Science, 302, 841). Intriguingly, certain polymorphisms within the promoter region of the SNCA gene have also been linked to increased risk for sporadic, late-onset PD (Pals et al., (2004) Ann. Neurol., 56, 591-5; Maraganore et al., (2006) JAMA, 296, 661-70).

Neuropathological evidence indicates that the intra-neuronal inclusions termed Lewy bodies and Lewy neurites, which represent one of the pathological hallmarks of PD and DLB seen at autopsy, contain high levels of aggregated α-synuclein protein (Spillantini et al., (1998) Proc. Natl. Acad. Sci., U.S.A., 95, 6469-73; Baba et al., (1998) Am. J. Pathol., 152, 879-884). These aggregates are generally viewed as the result of cellular mis-handling of α-synuclein protein (possibly related to post-translational events, such as hyper-phosphorylation (Anderson et al., (2006), J. Biol. Chem., 281, 29739-29752) and intracellular accumulation as both soluble toxic oligomers and insoluble fibrils (Sharon et al., (2001), P.N.A.S., 98, 9110-9115).

In addition, biochemical evidence suggests that overexpression of α-synuclein in cellular or animal systems may cause cellular stress and/or eventual death through a variety of mechanisms, including—among others—excess dopamine concentration and reactive oxygen species generation (Tabner et al., (2002), Free Radic. Biol. Med., 32(11):1076-83; Fahn et al., (1992), Ann. Neurol., 32, 804-12) as well as mitochondrial dysfunction (Lee (2003), Antioxid. Redox Signal, 5:337-48; Hashimoto et al., (2003), Neuromolecular Med., 4(1-2):21-36). Published PCT patent application WO 07084737 discloses treating lysosomal storage disorders having central nervous system implications with lysosomal enzymes.

SUMMARY

The invention is based, at least in part, on the discovery that certain agents, including acid-beta-glucocerebrosidase (GBA) polypeptides and select members of the cathepsin family of proteases (e.g., cathepsin D) can reduce the intracellular levels of alpha-synuclein (αS) within elements of the central and/or peripheral nervous system. As a result, the invention includes, inter alia, new methods of treating synucleinopathies, e.g., primary synucleinopathies, in subjects without a known classical lysosomal storage disorder, e.g., by administering a non-protease-type lysosomal enzyme polypeptide, e.g., a lipid-metabolizing enzyme, such as a GBA polypeptide, or a nucleic acid molecule that encodes a GBA polypeptide, or agents that activate GBA activity, or a protease-type lysosomal enzyme that has alpha-synuclein-lowering activity ("synucleinase" activity).

In general, protease-type lysosomal enzymes fall into the categories of aspartyl proteases (such as a cathepsin D or cathepsin E), and cysteinyl proteases (e.g., cathepsin F and cathepsin L). Therefore, the invention also includes, inter alia, new methods of treating synucleinopathies with protease-type lysosomal enzymes as well as procathepsin D, E, F, and L polypeptides, or nucleic acid molecules that encode cathepsin D, E, F, or L, or those that encode their pro- and pre-pro-protein polypeptide forms.

In addition, non-protease enzymes, e.g., GBA polypeptides, or protease enzymes, such as cathepsin D polypeptides, can be co-administered with agents that enhance or induce autophagy, such as rapamycin or rapamycin analogs.

Moreover, given the pivotal roles that prosaposin (PS) and its derivatives, saposin A (SA), saposin B (SB), saposin C (SC), and saposin D (SD), play as co-factors in the activity of GBA in vivo, other therapeutic methods include administering GBA polypeptides together with GBA-activating polypeptides, such as PS polypeptides and/or SC polypeptides; or administering PS polypeptides and/or SC polypeptides alone (to activate or enhance endogenous GBA) to facilitate a reduction in α-synuclein steady-state protein levels in vivo.

In general, the invention features methods of treating subjects, e.g., humans or animals, such as domesticated animals, e.g., dogs, cats, horse, goats, cows, and pigs, with a synucleinopathy, e.g., a primary or secondary synucleinopathy, but not a clinically diagnosed, or not a clinically diagnosable, lysosomal storage disease. These methods include administering to a subject any one or more of: a lysosomal enzyme polypeptide (e.g., a non-protease-type polypeptide such as GBA or a protease-type enzyme polypeptide such as cathepsin D), a polynucleotide encoding one or more lysosomal enzyme polypeptides, a lysosomal enzyme activating agent, and a polynucleotide encoding a lysosomal enzyme activating agent, in an amount effective to reduce a level of α-synuclein in the subject's central or peripheral nervous system, or both, or in the subject's lysosomal compartment.

The synucleinopathy can be any one or more of: Parkinson's disease (PD); sporadic or heritable dementia with Lewy bodies (DLB); pure autonomic failure (PAF) with synuclein deposition; multiple system atrophy (MSA); hereditary neurodegeneration with brain iron accumulation; and incidental Lewy body disease of advanced age. In other embodiments, the synucleinopathy can be any one or more of: Alzheimer's disease of the Lewy body variant; Down's syndrome; progressive supranuclear palsy; essential tremor with Lewy bodies; familial parkinsonism with or without dementia; tau gene and progranulin gene-linked dementia with or without parkinsonism; Creutzfeldt Jakob disease; bovine spongiform encephalopathy; secondary Parkinson disease; parkinsonism resulting from neurotoxin exposure; drug-induced parkinsonism with α-synuclein deposition; sporadic or heritable spinocerebellar ataxia; amyotrophic lateral sclerosis (ALS); and idiopathic rapid eye movement sleep behavior disorder.

In these methods, the protease-type lysosomal enzyme can be an aspartyl protease polypeptide, such as a cathepsin D polypeptide, a procathepsin D polypeptide, a cathepsin E polypeptide, and a procathepsin E polypeptide, or cysteinyl protease polypeptide, such as cathepsin F polypeptide, a procathepsin F polypeptide, a cathepsin L polypeptide, and a procathepsin L polypeptide.

In certain embodiments, the lysosomal enzyme activating agent is or includes a GBA polypeptide activating agent, such as isofagomine (IFG), or activating polypeptide, such as any one or more of a prosaposin polypeptide, a saposin A polypeptide, a saposin B polypeptide, a saposin C polypeptide, and a saposin D polypeptide. Of course, a polynucleotide encoding any one or more of a prosaposin polypeptide, a saposin A polypeptide, a saposin B polypeptide, a saposin C polypeptide, and a saposin D polypeptide can also be used.

In another aspect, the invention features methods of treating synucleinopathies, as described herein, and by further administering one or more agents that enhance autophagy of the α-synuclein. For example, the agent can be or include an mTOR inhibitor, rapamycin, a rapamycin analog, everolimus, cyclosporine, FK506, hsc70, N-octyl-4-epi-β-valienamine, or glycerol.

In the methods described herein, the agents can be a small molecule, a large molecule, a peptide, an antibody, a nucleic acid, or a biologically active fragment thereof.

In another aspect, the invention includes the use of any one or more of a lysosomal enzyme polypeptide, a polynucleotide encoding one or more lysosomal enzyme polypeptides, a lysosomal enzyme activating agent, and a polynucleotide encoding a lysosomal enzyme activating agent, as described herein, in methods of preparing medicaments for the treatment of a synucleinopathy, using well known methods of manufacture.

By "polypeptide" is meant any chain of amino acids, regardless of length or post-translational modification (e.g., glycosylation or phosphorylation), and thus includes proteins, polypeptides, and peptides.

By a "substantially pure polypeptide" is meant a polypeptide that has been separated from components which accompany it in vivo. A polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, of the desired polypeptide.

A "GBA polypeptide" is any GBA protein or polypeptide that has at least 50 percent of the biological activity of the corresponding wild-type GBA in reducing a level of αS in a dopaminergic cell model as described herein.

A "cathepsin polypeptide," such as a cathepsin D polypeptide is any cathepsin protein or polypeptide that has at least 50 percent of the biological activity of the corresponding wild-type cathepsin in reducing a level of αS in a dopaminergic cell model as described herein.

An "alpha-synuclein" protein or polypeptide (αS or αS protein), as used herein, includes a single, monomeric protein or polypeptide, as well as such αS proteins and polypeptides in the form of oligomers, e.g., in the form of dimers or trimers, or in the form of lipid-associated complexes, or lipid-free forms, or in the form of aggregates, and any of these forms can be soluble or insoluble. The terms also include the αS proteins found in complexes with other molecules.

In another aspect, the invention features methods for identifying candidate compounds for treating a synucleinopathy, including (a) obtaining a model system, e.g., a cellular system, such as a dopaminergic cell model, e.g., as described herein, facilitating the quantification of α-synuclein complexes; (b) contacting the model system with a test compound for incubation; and (c) comparing a level of α-synuclein in the presence and in the absence of the test compound; wherein a decrease in the level of α-synuclein complexes in the presence of the test compound indicates the test compound is a candidate compound for treating a synucleinopathy. In some embodiments, the precise quantification of α-synuclein protein is accomplished by the employment of a sandwich-type, specific and sensitive ELISA, e.g., as described herein. The α-synuclein model system can be, e.g., a protein-expressing cell or an animal model.

The invention also features methods of treating synucleinopathies, wherein the number or concentration of glucosylceramide and glucosylceramide-containing glycosphingolipids is reduced within neural and non-neural cells by targeting glucosylceramide and glucosylceramide-containing glycosphingolipids with proteins, peptide sequences, enzymes, antibodies, natural lipids, semi-synthetic lipids, and synthetic lipids as well as derivatives thereof. For example, the number or concentration of glucosylceramide and glucosylceramide-containing glycosphingolipids may be reduced within neural and non-neural cells by enzymatic or non-enzymatic hydrolysis of glucosylceramide and glucosylceramide-containing glycosphingolipids. Such methods can be catalyzed by GBA in either a wild-type form or in a mutant form that is binding-competent, but catalytically inactive. In these methods, prosaposin and/or its derivatives, such as saposin C, as described herein can also be administered. In some embodiments, the desired protein or polypeptide, such as GBA, is obtained expression of a polynucleotide encoding the enzyme or a derivative thereof.

In these methods, the agents, such as prosaposin, saposin A, saposin B, saposin C, saposin D, peptides derived thereof, small- or large molecules, antibodies, fragments of antibodies or small or large polynucleotides that improve the natural biological function of GBA, e.g., GBA activating agents, are delivered to the central and/or peripheral nervous system in an amount effective to decrease a level of αS protein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
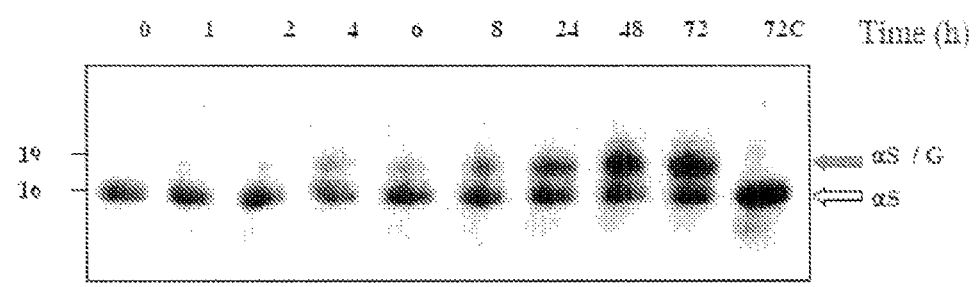
FIG. 1 is a representation of a Western Blot, demonstrating the time dependent formation of a stable 19-20 kDa complex (αS/G) between human brain gangliosides and α-synuclein in vitro.

In general, the invention relates to methods of reducing the levels of αS in cells in human or animal subjects who have a synucleinopathy that is not a lysosomal storage disorder, e.g., subjects who have primary (or invariable) synucleinopathy. These methods include, for example, administering non-protease-type lysosomal enzyme polypeptides, such as GBA polypeptides, or protease-type lysosomal enzyme polypeptides, such as cathepsin D polypeptides, or nucleic acid molecules that encode such polypeptides, either alone or in combination with agents that enhance or induce autophagy, such as rapamycin or a rapamycin analog. In addition, other GBA-activating agents, such as prosaposin polypeptides and/or saposin C polypeptides can be administered, or prosaposin polypeptides and/or saposin C polypeptides can be administered alone (to enhance activation of endogenous GBA activity) to facilitate a reduction in αS steady-state protein levels in vivo.

Thus, the present invention involves modulating the physiological degradation of α-synuclein (αS) by enhancing the processing within the lysosomes and/or the cytoplasm, and, in some embodiments, by enhancing the amount of αS taken up by the lysosomes (autophagy). While not wishing to be bound by any theory of operation, the degradative processing of αS aggregates is a system functioning at a steady-state level. By applying the law of mass action to the steady state degradative processing of αS proteins, oligomeric forms, aggregates, and/or complexes, one can modulate the degradative process towards its end products by increasing the abundance of its educts. By altering the component reactions of the pathway one can push the overall processing toward higher product levels. Thus, by either increasing the input of αS into lysosomes or enhancing the degradation efficiency itself, one can push the hydrolysis and subsequent processing of αS to a higher product level. Increasing both the autophagic component and the lysosomal component of the pathway can lead to increased protection from αS protein damage, and such combinations can achieve greater than additive effects.

Some embodiments described herein are methods of treating or delaying the progression or development of a synucleinopathy disorder that is not a lysosomal storage disease, e.g., by administering an agent or agents that increases the activity or level of GBA and/or prosaposin/saposin C. In some embodiments, the agents can be GBA and/or prosaposin/saposin C polypeptides or active fragments thereof, or nucleic acids encoding such polypeptides or active fragments. In some embodiments, the agent is a binding-competent, but catalytically inactive form of GBA, or a nucleic acid molecule encoding the same.

Other embodiments described herein are methods of treating or delaying the progression or development of a synucleinopathy disorder, e.g., by administering an agent or agents that increases the activity or level of cathepsin D or cathepsin F and/or preprocathepsin D or preprocathepsin F. In some embodiments, the agents can be GBA and/or prosaposin/saposin C/cathepsin D/cathepsin F polypeptides or active fragments thereof, or nucleic acids encoding such polypeptides or active fragments. In some embodiments, the agent is a binding-competent, but catalytically inactive form of GBA, cathepsin D or cathepsin F, or a nucleic acid molecule encoding the same.

Methods of Treating Synucleinopathy Disorders

The term synucleinopathy is used herein to name a group of neurodegenerative disorders characterized by the presence of increased levels, e.g., steady-state levels, of any one or more of soluble non-fibrillary variants, soluble oligomeric isoforms, insoluble non-fibrillary variants, complexes, and insoluble fibrillary aggregates of α-synuclein (αS) protein within cellular compartments of selective populations of neurons and glia. Thus, the αS steady-state level is understood to encompass all soluble as well as insoluble and intermediate (metastable) forms of the SNCA gene product.

These disorders include any one of the following grouped as "invariable" (or "primary") synucleinopathies (Schlossmacher M G. a—synuclein and synucleinopathies. The Dementias 2 Blue Books of Practical Neurology; Editors: Growdon J H & Rossor M N. Butterworth Heinemann, Inc., Oxford. 2007; Chapter 8: pp 184-213): Parkinson's disease (PD) e.g., sporadic Parkinson disease/parkinsonism and familial Parkinson disease/parkinsonism; sporadic or heritable dementia with Lewy bodies (DLB) (aka diffuse Lewy body disease); pure autonomic failure (PAF) with synuclein deposition; multiple system atrophy (MSA) (of cerebellar, parkinsonian, or mixed type); hereditary neurodegeneration with brain iron accumulation (aka, Hallervordern Spatz disease or pantothenate kinase 2-linked neurodegeneration); and incidental Lewy body disease of advanced age.

Furthermore, "variable" (or "secondary") synucleinopathies have been identified, where dysregulation of the alpha-synuclein metabolism is recognized to be a secondary event (given the abundance of the protein in the nervous system), which nevertheless contributes significantly to the course, penetrance, age-of-onset, severity and expressivity of the primary illness. Disorders with variable synucleinopathy (Schlossmacher M G. a—synuclein and synucleinopathies. The Dementias 2 Blue Books of Practical Neurology; Editors: Growdon J H & Rossor M N. Butterworth Heinemann, Inc., Oxford. 2007; Chapter 8: pp 184-213) include, but are not limited to, Alzheimer's disease of the Lewy body variant; Down's syndrome; progressive supranuclear palsy; essential tremor with Lewy bodies; familial parkinsonism with or without dementia resulting from a mutant gene and loci where no gene mutation has yet been identified; Creutzfeldt Jakob disease and related prion diseases such as bovine spongiform encephalopathy (mad cow disease); secondary Parkinson disease/parkinsonism resulting from neurotoxin exposure/drug-induced parkinsonism with α-synuclein deposition; sporadic or heritable spinocerebellar ataxia; amyotrophic lateral sclerosis (ALS); idiopathic rapid eye movement sleep behavior disorder; and other conditions associated with central and/or peripheral α-synuclein accumulation in mammals accompanying a primary disease process.

Clinically, all of these related disorders are characterized by a chronic and progressive decline in motor, cognitive, behavioral, and/or autonomic functions, depending on the distribution of the alpha-synuclein abnormalities.

A synucleinopathy may or may not be associated with disease symptoms. It may also be the product of normal aging. For example, persons over 55, 60, 65, 70, 75, or 80, may accumulate such αS proteins, e.g., in the form of aggregates, without obvious association with a pathology, symptom, or disease state. This condition is referred to as incidental Lewy body disease (see above) and people with this condition are considered to be at higher risk for PD/parkinsonism.

In general, subjects with the types of synucleinopathies contemplated herein do not have a clinically diagnosed (or not clinically diagnosable) primary lysosomal storage disorder (LSD), such as Gaucher disease or Tay-Sachs disease; these LSD syndromes often demonstrate an autosomal recessive inheritance pattern. However, subjects with single allele mutations in a gene that has been otherwise linked to a classical LSD phenotype may also develop synucleinopathy and suffer from its consequences (such as PD/parkinsonism or dementia with Lewy bodies), but without evidence of a systemic LSD (Eblan et al., N. Engl. J. Med., 2005).

LSDs are a group of metabolic disorders including over forty genetic disorders, many of which involve genetic defects in various lysosomal hydrolases that are commonly caused by mutations in both alleles of the gene that codes for the lysosomal enzyme. The hallmark feature of LSDs is the loss of 90 percent (or more) in enzymatic activity of the lysosomal hydrolase in question and the resulting abnormal accumulation of metabolites within lysosomes, which leads to the formation of large numbers of distended lysosomes in the perikaryon.

The methods described herein can be used to treat all persons with primary or secondary synucleinopathies, including those without mutations in their lysosomal enzyme genes, such as the GBA gene (i.e., sporadic Parkinson disease patients without a known single gene abnormality). These are patients where aging/toxic insult/head trauma/influence of modifier genes or other unknown causes may work together to cause or promote disease (Klein and Schlossmacher, Neurology, 2007, 69(22):2093-104).

The new methods described herein can also be used to treat a sub-population of synucleinopathy patients with a heterozygous (i.e., single allele rather than two allele) mutation in one or more of the lysosomal enzyme genes, e.g., in the GBA gene. These subjects are not suffering from a typical LSD (because they do not have a 90 percent or greater enzyme deficiency, because they still express enough GBA from the one remaining healthy allele), but they often suffer from a primary synucleinopathy. The currently available data suggest that this heterozygous mutation in GBA serves as a risk factor for Parkinson disease (and related disorders) and as a risk allele for the development of a primary synucleinopathy in the nervous system (Clark et al., Neurology, 2007, 69(12): 1270-7). Intriguingly, if both copies (alleles) of the GBA gene are mutated (for example in carriers of N370S, L444P, K198T, and R329c variants of GBA), a subgroup of patients with the classical LSD features of Gaucher disease will develop secondary synucleinopathy (Lwin et al., Mol. Genet. Metab., 2004, 81(1):70-3).

In particular, the treatments can be applied prophylactically to those people who are genotyped for known GBA mutations (who, for example, have already been genotyped due to a family history of Gaucher Disease) to prevent the development of Parkinson disease or therapeutically in those people with known GBA mutations who have already developed a synucleinopathy disorder. Thus, the step of genotyping the patient or subject for a mutation in a lysosomal enzyme gene, e.g., the GBA gene, can be a first step in the therapeutic methods described herein. Patients who are heterozygotes for the mutation, are candidates for treatment by the new methods.

Administering or Activating Non-Protease-Type Lysosomal Enzyme Polypeptides

The new methods include administering non-protease-type lysosomal enzyme polypeptides, e.g., GBA polypeptides, either directly, or by administering nucleic acid molecules that encode GBA polypeptides, to patients in need thereof, e.g., in subjects having been diagnosed with a synucleinopathy that is not a lysosomal storage disorder.

GBA is also known as glucosidase, beta, acid; acid beta-glucosidase; acid beta-glucosidase; glucocerebrosidase; glucosylceramidase; and GBAP. This gene normally encodes a lysosomal membrane protein that cleaves the beta-glucosidic linkage of glucosylceramide (also known as glucocerebroside), an intermediate in glycolipid metabolism. It can also cleave glucosylsphingosine as a secondary substrate to generate glucose and sphingosine (Sidransky, Mol Genet Met, 2004, pp 6-15). Mutations in this gene can cause Gaucher disease, a lysosomal storage disease characterized by an accumulation of glucocerebrosides and glucosylsphingosines. Alternative splicing results in multiple transcript variants encoding the same protein. There are five mRNA variants (which vary in the 5' UTR), the longest of which is set forth in the GenBank database at Accession Nos. NM_001005749.1 (mRNA) and NP_001005749.1 (amino acid). Information regarding GBA can be found in the Entrez Gene database at GeneID: 2629.

The methods can also include increasing activation of the administered GBA polypeptides or any endogenous GBA by administering GBA-activating polypeptides, such as prosaposin (PS) and/or its derivatives, saposin A (SA), saposin B (SB), saposin C (SC), and saposin D (SD).

The prosaposin gene encodes a highly conserved glycoprotein which is either secreted as a full length protein with neurotrophic activities, or proteolytically processed in endosomal/lysosomal compartments by cathepsin D and other proteases into the 4 saposins A, B, C and D (Leonova et al., J. Biol. Chem., 1996, 271:17312-17320; Hiraiwa et al., Arch. Biochem. Biophys., 1997, 341:17-24). Saposins A-D localize primarily to the lysosomal compartment where they facilitate the catabolism of glycosphingolipids with short oligosaccharide groups. Saposin C functions to anchor the GBA protein under low pH conditions to the internal side of the lysosomal membrane, thus allowing GBA to fold properly for correct substrate interaction (Salvioli et al., 2000, FEBS. Lett. 472: 17-21). Furthermore, saposin C protects the GBA protein from proteolytic degradation by lysosomal proteases (Sun et al., J. Biol. Chem., 2003, 278:31918-31923). The biological importance of this protein is underscored by the fact that null mutations in the prosaposin gene and/or point mutations in the Saposin C region of the gene can lead to clinical Gaucher Disease, despite the presence of wild type GBA (Pamplos et al., Acta. Neuropathol., 1999, 97:91-97; Tylki-Szymanska, 2007, Clin. Genet., 72:538-542; Rafi et al., 1993, Somat. Cell Mol. Genet., 19:1-7).

Furthermore, the low activity in vivo of the most common GBA mutation, N370S, can be accounted for by its inability to interact with saposin C and anionic phospholipids (Salvioli et al., Biochem. J., 2005, 390:95-103). Alternative splicing of prosaposin results in multiple transcript variants encoding different isoforms. Prosaposin (variant Gaucher disease and variant metachromatic leukodystrophy) is described in the Entre Gene database at GeneID: 5660. The sequences of its isoforms are available in GenBank as follows: prosaposin isoform a preproprotein: NM_002778.2 (mRNA) and NP_002769.1 (amino acid); prosaposin isoform b preproprotein: NM_001042465.1 (mRNA) and NP_001035930.1 (amino acid); and prosaposin isoform c preproprotein NM_001042466.1 (amino acid) and NP_001035931.1 042465.1 (mRNA).

Both the GBA polypeptides and GBA encoding nucleic acid molecules, as well as the GBA-activating polypeptides and corresponding nucleic acid molecules, can be administered using known techniques, including the techniques described herein. For example, the GBA polypeptide encoding nucleic acid molecules can be administered using gene therapy as described herein.

Administering Protease-Type Lysosomal Enzyme Polypeptides

In an alternative method, a subject diagnosed as having a synucleinopathy that is not a LSD, can be treated with a lysosomal protease polypeptides, such as a cathepsin D polypeptide. Such proteases can be administered directly, or by administering a nucleic acid molecule that encodes the desired protease.

In general, protease-type lysosomal enzymes fall into the categories of aspartyl proteases such as a cathepsin D (or cathepsin E), and cysteinyl proteases (e.g., cathepsin F and cathepsin L). Therefore, the invention includes, inter alia, new methods of treating synucleinopathies with protease-type lysosomal enzymes related to procathepsin D or procathepsin E polypeptide, or alternatively with protease-type lysosomal enzymes related to procathepsin F or procathepsin L polypeptide, or nucleic acid molecules that encode a cathepsin D, cathepsin E, cathepsin F, or cathepsin L, or those that encode their pre-pro-protein polypeptide forms.

The cathepsin family of proteases includes approximately a dozen members, which are distinguished by their structure and the proteins they cleave. Most of the members become activated at the low pH found in lysosomes. Thus, the activity of this family lies almost entirely within those organelles. The cathepsin D gene (CTSD) encodes a lysosomal aspartyl protease composed of a dimer of disulfide-linked heavy and light chains, both produced from a single protein precursor. This proteinase, which is a member of the peptidase C1 family, has a specificity similar to, but narrower than, that of pepsin A. Sequence information of the human gene is available in GenBank as *Homo sapiens* cathepsin D (CTSD), mRNA: NM_001909.

Within the cathepsin family, only one other known member (besides cathepsin D) possesses aspartyl protease activity, that is cathepsin E. It is transcribed in 2 variants. Sequence information for the human variants is available in GenBank as *Homo sapiens* cathepsin E (CTSE), mRNA: NM_001910.2 and NM_148964.1.

Within the cathepsin family, various other members possess cysteine protease activity, for example cathepsins C, L, F and W. Of these many cysteine protease cathepsins, the F and W enzymes form a separate subgroup, based on their chromosomal locations, sequence homology and splicing pattern (Wex et al., 1999, Biochem. Biophys. Res. Commun., 259: 401-407). Cathepsin F is expressed in brain, as well as heart, skeletal muscle and other tissues (Wang et al., 1998, J. Biol. Chem., 273:32000-32008). Knock out of the cathepsin F gene in mice leads to a late onset neurological disease with gliosis, neuronal loss and accumulation of autofluorescent granules (Tang et al., 2006, Mol. Cell. Biol., 26:2309-2316), which is thought to be a model of human adult-onset neuronal ceroid lipofuscinosis. Sequence information of the human gene is available in GenBank as *Homo sapiens* cathepsin E (CTSE), mRNA: NM_003793.3.

Both the cathepsin D or F polypeptides and cathepsin D or F encoding nucleic acid molecules can be administered using known techniques, including the techniques described herein. For example, the cathepsin D encoding nucleic acid molecules can be administered using gene therapy as described herein.

Administering Other Lysosomal Enzyme Polypeptides

Examples of other polypeptides that can be administered to enhance the degradative processing of αS within lysosomes include Aspartylglucosaminidase; α-Galactosidase A; Palmitoyl Protein Thioesterase; Tripeptidyl Peptidase; Lysosomal Transmembrane Protein; Cysteine transporter; Acid ceramidase; Acid α-L-fucosidase; Protective protein/cathepsin A; Acid β-galactosidase; Iduronate-2-sulfatase; α-L-Iduronidase; Galactocerebrosidase; Acid α-mannosidase; Acid β-mannosidase; Arylsulfatase B; Arylsulfatase A; N-Acetylgalactosamine-6-sulfate; Acid β-galactosidase; N-Acetylglucosamine-1-phosphotransferase; Acid sphingomyelinase; NPC-1; α-glucosidase; β-Hexosaminidase B; Heparan N-sulfatase; α-N-Acetylglucosaminidase; Acetyl-CoA: α-glucosaminide; N-Acetylglucosamine-6-sulfate; α-N-

Acetylgalactosaminidase; α-N-Acetylgalactosaminidase; α-Neuramidase; β-Glucuronidase; β-Hexosaminidase A; glucocerebrosidase; ubiquitin C-terminal hydrolase-L1; and Acid Lipase.

The proteins and polypeptides can be lysosomal degradation enzymes or non-lysosomal proteins that promote degradation of synuclein or synuclein aggregates. These proteins and their coding sequences are well known in the art. Typically the human forms of the proteins and their coding sequences will be used, although for work in animal models, the animal orthologs may be desirable. One or more of such enzymes can be used.

Enhancing and Inducing Autophagy of Alpha-Synuclein

In another aspect of the invention, agents that enhance and/or induce autophagy, such as rapamycin or rapamycin analogs are co-administered with lysosomal enzymes, e.g., GBA polypeptides, or non-GBA-type lysosomal proteases, such as cathepsin D polypeptides, to achieve a greater than additive therapeutic effect.

Autophagy is a catabolic process involving the degradation of a cell's own components through the lysosomal machinery. It is a tightly-regulated process that plays a normal part in cell growth, development, and homeostasis, helping to maintain a balance between the synthesis, degradation, and subsequent recycling of cellular products. It is a major mechanism by which a starving cell reallocates nutrients from unnecessary processes to more-essential processes.

A variety of autophagic processes exist, all having in common the degradation of intracellular components via the lysosome. The most well-known mechanism of autophagy involves the formation of a membrane around a targeted region of the cell, separating the contents from the rest of the cytoplasm. The resultant vesicle then fuses with a lysosome and subsequently degrades the contents.

Autophagy can be broadly separated into three types: macroautophagy, microautophagy, and chaperone-mediated autophagy: (i) macroautophagy involves the formation of a de-novo-formed membrane sealing on itself to engulf cytosolic components (proteins and/or whole organelles), which are degraded after its fusion with the lysosome; (ii) microautophagy is the direct invagination of materials into the lysosome; and (iii) chaperone-mediated autophagy (CMA) involves the degradation of specific cytosolic proteins marked with a specific peptide sequence. CMA is very selective in what is degraded and degrades only certain proteins and not organelles. CMA is responsible for the degradation of approximately 30% of cytosolic proteins in tissues such as liver, kidney and in many types of cultured cells.

Chaperone molecules bind to and transport marked proteins to the lysosome via a receptor complex. In CMA, only those proteins that have a consensus peptide sequence get recognized by the binding of a chaperone. This CMA substrate/chaperone complex then moves to the lysosomes, where a CMA receptor lysosome-associated membrane protein recognizes the complex; the protein is unfolded and translocated across the lysosome membrane assisted by additional proteins on the inside. Soluble wild-type α-synuclein has been reported to be degraded by this mechanism (Cuervo et al. (2004), Science, 305:1292).

Autophagy is part of everyday normal cell growth and development wherein the mammalian target of rapamycin (mTOR) plays an important regulatory role. Starvation inhibits mTOR activity, provoking various cellular responses, including cell arrest in the early G1 phase, inhibition of protein synthesis, nutrient transporter turnover, transcriptional changes, and autophagy. Rapamycin is a well known agent for the inhibition of mTOR activity. Any rapamycin analog or mTOR inhibitor known in the art can be used for the methods described herein. For example, everolimus, cyclosporine, and FK506 can be used or tested for their autophagy stimulatory capacity. Although all of such analogs and inhibitors may not have the autophagy stimulatory activity of rapamycin, this activity can be readily determined among these compounds. The agents that promote autophagy include chaperone proteins and compounds that bind to and escort substrates to the lysosome. Other compounds that can stimulate autophagy include hsc70, N-octyl-4-epi-β-valienamine, and glycerol. One or more of such agents can be used in the methods of enhancing autophagy described herein.

Any lysosomal enzyme that helps to degrade synuclein or cause disaggregation of synuclein complexes, alone or in combination with other lysosomal enzyme(s) or agent(s), can be used for the present invention.

Methods of Administration

Generally, the methods described herein include administering a therapeutically effective amount of a therapeutic compound as described herein, to a subject who is in need of, or who has been determined to be in need of, such treatment.

As used in this context, to "treat" means to ameliorate at least one symptom of the synucleinopathy disorder and/or to cause a measurable decrease in the level of αS protein in the subject. Similarly, administration of a "therapeutically effective amount" or "effective amount" of a composition described herein for the treatment of a synucleinopathy will result in a decreased level of αS protein and/or results in an improvement in one or more symptoms of the synucleinopathy disorder. This amount can be the same or different from a "prophylactically effective amount," which is an amount necessary to inhibit, e.g., prevent, onset of disease or disease symptoms.

An effective amount can be administered in one or more administrations, applications, or dosages. A therapeutically effective amount of a composition depends on the composition selected. The compositions can be administered from one or more times per day to one or more times per week; including once every other day. The skilled artisan will appreciate that certain factors influence the dosage and timing required to effectively treat a subject, including, but not limited to, the severity of the disease or disorder, previous treatments, the general health and/or age of the subject, and other diseases present. Moreover, treatment of a subject with a therapeutically effective amount of the compositions described herein can include a single treatment or a series of treatments.

Dosage, toxicity, and therapeutic efficacy of the compounds can be determined, e.g., by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

More specific information on dosages is discussed below.

Administration of Polypeptides and Small Molecules

Agents that cross the blood-brain barrier can be administered systemically, if desired. Alternatively, agents such as the polypeptides and small molecules described herein, can be delivered directly to a site in the body where cells display αS accumulation. Such agents that do not cross the blood brain barrier can be administered to the brain, for example, using direct injection facilitated by stereotactic guidance. Such agents can also be administered via intraventricular or intraparenchymal routes.

In other embodiments, nucleic acid molecules encoding the desired polypeptides can be delivered, e.g., in the form of a viral vector containing a polypeptide-encoding gene. The viral delivery may be under conditions that favor expression of the transgene in specific central or peripheral nerve cells, such as ependymal or other glial cells that line the ventricles of the brain. Ependymal cells can be transduced to express the transgene and secrete the encoded protein product into the cerebrospinal fluid (CSF).

The polypeptides described herein can be incorporated into a pharmaceutical composition useful to treat, e.g., inhibit, attenuate, prevent, or ameliorate, a synucleinopathy. The pharmaceutical composition can be administered to a subject suffering from a synucleinopathy disorder or someone who is at risk of developing said deficiency. The compositions should contain a therapeutic or prophylactic amount of the polypeptide, in a pharmaceutically-acceptable carrier. The pharmaceutical carrier can be any compatible, non-toxic substance suitable to deliver the polypeptides to the patient. Sterile water, alcohol, fats, and waxes may be used as the carrier. Pharmaceutically-acceptable adjuvants, buffering agents, dispersing agents, and the like, may also be incorporated into the pharmaceutical compositions. The carrier can be combined with the polypeptide in any form suitable for administration by intraventricular injection or infusion (which form can also be suitable for intravenous or intrathecal administration) or otherwise.

Suitable carriers include, for example, physiological saline, bacteriostatic water, Cremophor EL® (BASF, Parsippany, N.J.) or phosphate buffered saline (PBS), other saline solutions, dextrose solutions, glycerol solutions, water and oils emulsions such as those made with oils of petroleum, animal, vegetable, or synthetic origin (peanut oil, soybean oil, mineral oil, or sesame oil). In some embodiments, an artificial CSF is used as a carrier. In general, the carrier will be sterile and free of pyrogens. The concentration of the polypeptide in the pharmaceutical composition can vary widely, i.e., from at least about 0.01% by weight, to 0.1% by weight, to about 1% weight, to as much as 20% by weight or more of the total composition.

For intraventricular administration of the polypeptides described herein, or other agents, the composition must be sterile and should be a fluid. It must be stable under the conditions of manufacture and storage and must be preserved against the contaminating action of microorganisms such as bacteria and fungi. Prevention of the action of microorganisms can be achieved by various antibacterial and antifungal agents, for example, parabens, chlorobutanol, phenol, ascorbic acid, thimerosal, and the like. In many cases, it will be useful to include isotonic agents, for example, sugars, polyalcohols such as mannitol, sorbitol, and sodium chloride in the composition.

The rate of administration is such that the administration of a single dose can be administered as a bolus. A single dose can also be infused over about 1-5 minutes, about 5-10 minutes, about 10-30 minutes, about 30-60 minutes, about 1-4 hours, or consumes more than four, five, six, seven, or eight hours. It may take more than 1 minute, more than 2 minutes, more than 5 minutes, more than 10 minutes, more than 20 minutes, more than 30 minutes, more than 1 hour, more than 2 hours, or more than 3 hours. While bolus intraventricular administrations are effective, slow infusions are particularly effective. Without being bound by any particular theory of operation, it is believed that the slow infusion is effective due to the turn-over of the CSF.

While estimates and calculations in the literature vary, the CSF is believed to turn over within about 4, 5, 6, 7, or 8 hours in humans. In one embodiment, the slow infusion time should be metered so that it is about equal to or greater than the turn-over time of the CSF. Turn-over time may depend on the species, size, and age of the subject, but can be determined using methods known in the art. The infusion may also be continuous over a period of one or more days. The patient can be treated once, twice, or three or more times a month, e.g., weekly, e.g., every two weeks. Infusions can be repeated over the course of a subject's life as dictated by re-accumulation of the disease's substrate in the brain or visceral organs. Re-accumulation can be determined by any of the techniques that are well known in the art for the identification and quantization of the relevant substrate, which techniques may be performed on one or more samples taken from the brain and/or from one or more of the visceral organs. Such techniques include enzymatic assays and/or immunoassays, e.g., radioimmunoassays or ELISAs.

Slow intraventricular infusion provides diminished amounts of the substrate for an administered polypeptide (e.g., an enzyme) in at least the brain and potentially in visceral organs. The reduction in a substrate such as aS protein accumulated in the brain, lungs, spleen, kidney, and/or liver may be dramatic. Reductions of greater that 10%, 20%, 30%, 40%, 50%, 60%, 70%, 80%, or 90% can be achieved. The reduction achieved is not necessarily uniform from patient to patient or even from organ to organ within a single patient. Reductions can be determined by any of the techniques that are well known in the art, e.g., by enzymatic assays and/or immunoassay techniques, as discussed elsewhere herein.

In an illustrative embodiment, the administration is accomplished by infusion of the polypeptide into one or both of the lateral ventricles of a subject or patient. By infusing into the lateral ventricles, the polypeptide is delivered to the site in the brain in which the greatest amount of CSF is produced. The polypeptide can also be infused into more than one ventricle of the brain. Treatment can consist of a single infusion per target site, or can be repeated. Multiple infusion/injection sites can be used. For example, the ventricles into which the polypeptide is administered can include the lateral ventricles and the fourth ventricle. In some embodiments, in addition to the first administration site, a composition containing the polypeptide is administered to another site which can be contralateral or ipsilateral to the first administration site. Injections/infusions can be single or multiple, unilateral or bilateral.

To deliver the solution or other composition containing the polypeptide specifically to a particular region of the central nervous system, such as to a particular ventricle, e.g., to the lateral ventricles or to the fourth ventricle of the brain, it can be administered by stereotaxic microinjection. For example, on the day of surgery, patients have a stereotaxic frame base fixed in place (screwed into the skull). The brain with stereotaxic frame base (MRI compatible with fiduciary markings) is imaged using high resolution MRI. The MRI images are then transferred to a computer that runs stereotaxic software. A series of coronal, sagittal, and axial images used to determine the target site of vector injection, and trajectory. The software directly translates the trajectory into 3-dimensional coordinates appropriate for the stereotaxic frame. Burr holes are drilled above the entry site and the stereotaxic apparatus localized with the needle implanted at the given depth. The polypeptide solution in a pharmaceutically acceptable carrier is then injected. Additional routes of administration can be used, e.g., superficial cortical application under direct visualization, or other non stereotaxic application.

One way to deliver a slow infusion is to use a pump. Such pumps are commercially available, for example, from Alzet (Cupertino, Calif.) or Medtronic (Minneapolis, Minn.). The pump may be implantable. Another convenient way to administer the enzymes is to use a cannula or a catheter. The cannula or catheter can be used for multiple administrations separated in time. Cannulae and catheters can be implanted stereotaxically. It is contemplated that multiple administrations will be used to treat the typical patient with a synucleinopathy disorder. Catheters and pumps can be used separately or in combination.

Administration of Nucleic Acid Molecules and Gene Therapy

The nucleic acid molecules described herein, such as nucleic acid molecules encoding GBA or cathepsin D polypeptides, can be delivered using a number of different methods. For example, gene transfer can be mediated by a DNA viral vector, such as an adenovirus (Ad) or adeno-associated virus (AAV). A vector construct refers to a polynucleotide molecule including the viral genome or part thereof and a transgene. Adenoviruses (Ads) are a relatively well characterized, homogenous group of viruses, including over 50 serotypes. See, e.g., International PCT Application No. WO 95/27071. Ads are easy to grow and do not require integration into the host cell genome. Recombinant Ad derived vectors, particularly those that reduce the potential for recombination and generation of wild-type virus, have also been constructed. See, International PCT Application Nos. WO 95/00655 and WO 95/11984. Wild-type AAV has high infectivity and specificity integrating into the host cell's genome. See, Hermonat and Muzyczka (1984) Proc. Natl. Acad. Sci., USA, 81:6466-6470 and Lebkowski et al. (1988) Mol. Cell. Biol., 8:3988-3996.

Suitable neurotrophic viral vectors to deliver the nucleic acid molecules described herein include, but are not limited to, adeno-associated viral vectors (AAV), herpes simplex viral vectors (U.S. Pat. No. 5,672,344) and lentiviral vectors.

In the new methods, AAV of any serotype or pseudotype can be used. The serotype of the viral vector used in certain embodiments of the invention is selected from the group consisting from AAV1, AAV2, AAV3, AAV4, AAV5, AAV6, AAV7, and AAV8 (see, e.g., Gao et al. (2002) PNAS, 99:11854 11859; and Viral Vectors for Gene Therapy: Methods and Protocols, ed. Machida, Humana Press, 2003). Other serotype besides those listed herein can be used. Furthermore, pseudotyped AAV vectors can also be utilized in the methods described herein. Pseudotyped AAV vectors are those that contain the genome of one AAV serotype in the capsid of a second AAV serotype; for example, an AAV vector that contains the AAV2 capsid and the AAV1 genome or an AAV vector that contains the AAV5 capsid and the AAV 2 genome (Auricchio et al., (2001) Hum. Mol. Genet., 10(26):3075-81).

AAV vectors are derived from single stranded (ss) DNA parvoviruses that are nonpathogenic for mammals (reviewed in Muzyscka (1992) Curr. Top. Microb. Immunol., 158:97-129). Briefly, AAV based vectors have rep and cap viral genes that account for 96% of the viral genome removed, leaving the two flanking 145 basepair (bp) inverted terminal repeats (ITRs), which are used to initiate viral DNA replication, packaging and integration. In the absence of helper virus, wild type AAV integrates into the human host cell genome with preferential site specificity at chromosome 19q13.3 or it can be maintained episomally. A single AAV particle can accommodate up to 5 kb of ssDNA, therefore leaving about 4.5 kb for a transgene and regulatory elements, which is typically sufficient. However, trans-splicing systems as described, for example, in U.S. Pat. No. 6,544,785, may nearly double this limit.

In an illustrative embodiment, AAV is AAV2. Adeno associated virus of many serotypes, especially AAV2, have been extensively studied and characterized as gene therapy vectors. Those skilled in the art are familiar with the preparation of functional AAV-based gene therapy vectors. Numerous references to various methods of AAV production, purification, and preparation for administration to human subjects can be found in the extensive body of published literature (see, e.g., Viral Vectors for Gene Therapy: Methods and Protocols, ed. Machida, Humana Press, 2003). Additionally, AAV based gene therapy targeted to cells of the CNS has been described in U.S. Pat. Nos. 6,180,613 and 6,503,888. Additional exemplary AAV vectors are recombinant AAV2/1, AAV2/2, AAV2/5, AAV2/6, AAV2/7, and AAV2/8 serotype vectors encoding human protein.

In certain methods described herein, the vector includes a transgene operably linked to a promoter. The transgene encodes a biologically active molecule, such as a GBA polypeptide, expression of which in the CNS results in at least partial correction of a synucleinopathy.

The level of transgene expression in eukaryotic cells is largely determined by the transcriptional promoter within the transgene expression cassette. Promoters that show long term activity and are tissue- and even cell-specific are used in some embodiments. Examples of promoters include, but are not limited to, the cytomegalovirus (CMV) promoter (Kaplitt et al. (1994) Nat. Genet., 8:148-154), CMV/human β3 globin promoter (Mandel et al. (1998) J. Neurosci., 18:4271-4284), GFAP promoter (Xu et al. (2001) Gene Ther., 8:1323-1332), the 1.8 kb neuron specific enolase (NSE) promoter (Klein et al. (1998) Exp. Neurol., 150:183-194), chicken beta actin (CBA) promoter (Miyazaki (1989) Gene, 79:269-277), the β-glucuronidase (GUSB) promoter (Shipley et al. (1991) Genetics, 10:1009-1018), and ubiquitin promoters such as those isolated from human ubiquitin A, human ubiquitin B, and human ubiquitin C, as described in U.S. Pat. No. 6,667,174. To prolong expression, other regulatory elements may additionally be operably linked to the transgene, such as, e.g., the Woodchuck Hepatitis Virus Post Regulatory Element (WPRE) (Donello et al. (1998) J. Virol., 72:5085-5092) or the bovine growth hormone (BGH) polyadenylation site.

For some CNS gene therapy applications, it may be necessary to control transcriptional activity. To this end, pharmacological regulation of gene expression with viral vectors can been obtained by including various regulatory elements and drug responsive promoters as described, for example, in Haberma et al. (1998) Gene Ther., 5:1604-16011; and Ye et al. (1995) Science, 283:88-91.

High titer AAV preparations can be produced using techniques known in the art, e.g., as described in U.S. Pat. No. 5,658,776 and Viral Vectors for Gene Therapy: Methods and Protocols, ed. Machida, Humana Press, 2003.

Dosages

For the treatment of disease, the appropriate dosage of a polypeptide, e.g., a GBA or cathepsin polypeptide or other agent described herein, will depend on the type of disease to be treated, the severity and course of the disease, whether the polypeptide or agent is administered for prophylactic or therapeutic purposes, previous therapy, the patient's clinical history and response to the enzyme or agent, and the discretion of the attending physician.

In a combination therapy regimen, the compositions described herein are administered in a therapeutically effective or synergistic amount. A therapeutically synergistic amount is that amount of one or more polypeptides or other agents in combination with one or more other polypeptides or agents, necessary to significantly reduce or eliminate conditions or symptoms associated with a particular disease in a manner that is more than additive when the two polypeptides/agents are administered alone.

While dosages may vary depending on the disease and the patient, the polypeptide is generally administered to the patient in amounts of from about 0.1 to about 1000 milligrams per 50 kg of patient each administration and may be repeated weekly, monthly, or at other time intervals as needed. In one embodiment, the polypeptide is administered to the patient in amounts of about 1 to about 500 milligrams per 50 kg of patient per month. In other embodiments, the polypeptide is administered to the patient in amounts of about 5 to about 300 milligrams per 50 kg of patient per month, or about 10 to about 200 milligrams per 50 kg of patient per month.

Depending on the type and severity of the disease, the polypeptide or agent can be administered so that the local concentration provided is about 100 pg/ml to about 100 µg/ml, 1 ng/ml to about 95 µg/ml, 10 ng/ml to about 85 µg/ml, 100 ng/ml to about 75 µg/ml, from about 100 ng/ml to about 50 µg/ml, from about 1 µg/ml to about 25 µg/ml, from about 1 µg/ml to about 15 µg/ml, from about 1 µg/ml to about 10 µg/ml, or from about 1 µg/ml to about 4 µg/ml.

When the polypeptide or agent is delivered by gene therapy through viral virions, the dose can be from about $2\times10^6$ to about $2\times10^{12}$ drp, from about $2\times10^7$ to about $2\times10^{11}$ drp, or from about $2\times10^8$ to about $2\times10^{11}$ drp (DNase resistant particles) per unit dose. In certain embodiments, the concentration or titer of the vector in the composition is at least: (a) 5, 6, 7, 8, 9, 10, 15, 20, 25, or 50 ($\times10^{12}$ gp/ml); (b) 5, 6, 7, 8, 9, 10, 15, 20, 25, or 50 ($\times10^9$ tu/ml); or (c) 5, 6, 7, 8, 9, 10, 15, 20, 25, or 50 ($\times10^{10}$ iu/ml).

The terms "genome particles (gp)," or "genome equivalents," as used in reference to a viral titer, refer to the number of virions containing the recombinant AAV DNA genome, regardless of infectivity or functionality. The number of genome particles in a particular vector preparation can be measured by procedures such as described in the Examples herein, or for example, in Clark et al. (1999) Hum. Gene Ther., 10:1031-1039; Veldwijk et al. (2002) Mol. Ther., 6:272-278.

The terms "infection unit (iu)," "infectious particle," or "replication unit," as used in reference to a viral titer, refer to the number of infectious and replication-competent recombinant AAV vector particles as measured by the infectious center assay, also known as replication center assay, as described, for example, in McLaughlin et al. (1988) J. Virol., 62:1963-1973.

The term "transducing unit (tu)" as used in reference to a viral titer, refers to the number of infectious recombinant AAV vector particles that result in the production of a functional transgene product as measured in functional assays such as described in Examples herein, or for example, in Xiao et al. (1997) Exp. Neurobiol., 144:113-124; or in Fisher et al. (1996) J. Virol., 70:520-532 (LFU assay).

When the polypeptide or agent is administered by protein or chemical therapy, the dose can be from about 0.1 mg to about 50 mg, from about 0.1 mg to about 25 mg, from about 0.1 mg to about 10 mg, from about 0.5 mg to about 5 mg, or from about 0.5 mg to about 2.5 mg per unit dose.

The polypeptides and agents described herein can be administered as a single dose or repeatedly. For repeated administrations over several days or longer, depending on the condition, the treatment is sustained until a desired suppression of disease symptoms occurs. The progress of the therapy of the invention is monitored by conventional techniques and assays.

Pharmaceutical Compositions

A "pharmaceutical composition" or "medicament" is intended to encompass a combination of an active component or agent, e.g., an enzyme polypeptide, and optionally a carrier or other material, e.g., a compound or composition, which is inert (for example, a detectable agent or label) or active, such as an adjuvant, diluent, binder, stabilizer, buffer, salt, lipophilic solvent, preservative, adjuvant or the like, or a mixture of two or more of these substances.

Carriers are preferably pharmaceutically acceptable. They may include pharmaceutical excipients and additives, proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term carrier also includes a buffer or a pH adjusting agent or a composition containing the same; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid, Tris, tromethamine hydrochloride, or phosphate buffers. Additional carriers include polymeric excipients/additives such as polyvinylpyrrolidones, ficolls (a polymeric sugar), dextrates (e.g., cyclodextrins, such as 2-hydroxypropyl-.quadrature.-cyclodextrin), polyethylene glycols, flavoring agents, antimicrobial agents, sweeteners, antioxidants, antistatic agents, surfactants (e.g., polysorbates such as "TWEEN 20"® and "TWEEN 80"®), lipids (e.g., phospholipids, fatty acids), steroids (e.g., cholesterol), and chelating agents (e.g., EDTA).

As used herein, the term "pharmaceutically acceptable carrier" encompasses any of the standard pharmaceutical carriers, such as saline, solvents, dispersion media, coatings, antibacterial and antifungal agents, isotonic and absorption delaying agents, and the like, a phosphate buffered saline solution, water, and emulsions, such as an oil/water or water/oil emulsion, and various types of wetting agents, compatible with pharmaceutical administration. Supplementary active compounds can also be incorporated into the compositions. The compositions and medicaments manufactured and/or used in accordance with the present invention and which include the particular polypeptides, nucleic acid molecules or other agents can include stabilizers and preservatives and any of the carriers described herein with the additional proviso that they be acceptable for use in vivo. For examples of additional carriers, stabilizers, and adjuvants, see Martin REMINGTON'S PHARM. SCI., 15th Ed. (Mack Publ. Co., Easton (1975) and Williams & Williams, (1995), and in the "PHYSICIAN'S DESK REFERENCE," 52nd ed., Medical Economics, Montvale, N.J. (1998).

The methods described herein include the manufacture and use of pharmaceutical compositions, which can include compounds identified by the screening methods described herein as active ingredients. Also included are the pharmaceutical compositions themselves. For example, the compositions described herein can include agents that increase the level or activity of one or both of GBA or PS/SC.

Pharmaceutical compositions are typically formulated to be compatible with their intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., the books in the series Drugs and the Pharmaceutical Sciences: a Series of Textbooks and Monographs (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injection can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel®, or corn starch; a lubricant such as magnesium stearate or Sterotes®; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

Therapeutic compounds that are or include nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., (1998) Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

Kits

Kits according to the present invention are assemblages of separate components. While they can be packaged in a single container, they can be subpackaged separately. Even a single container can be divided into compartments. Typically a set of instructions will accompany the kit and provide instructions for delivering the enzymes, e.g., the GBA polypeptides, intraventricularly. The instructions may be in printed form, in electronic form, as an instructional video or DVD, on a compact disc, on a floppy disc, on the internet with an address provided in the package, or a combination of these means. Other components, such as diluents, buffers, solvents, tape, screws, and maintenance tools can be provided in addition to the enzyme, one or more cannulae or catheters, and/or a pump.

Methods of Screening

Also included herein are methods for screening test compounds, e.g., polypeptides, polynucleotides, inorganic or organic large or small molecule test compounds, to identify agents useful in the treatment of synucleinopathy disorders that are not associated with a lysosomal storage disease, e.g., a primary synucleinopathy. In particular, the new screening assays are designed to locate new compounds that serve as GBA-activating agents for either wild-type or mutant forms of GBA.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, Solid-Supported Combinatorial and Parallel Synthesis of Small-Molecular-Weight Compound Libraries, Pergamon-Elsevier Science Limited (1998), and include those such as the "split and pool" or "parallel" synthesis techniques, solid-phase and solution-phase techniques, and encoding techniques (see, for example, Czarnik, (1997) Curr. Opin. Chem. Bio., 1:60-6). In addition, a number of small molecule libraries are commercially available. A number of suitable small molecule test compounds are listed in U.S. Pat. No. 6,503,713, incorporated herein by reference in its entirety Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample, e.g., a cell or living tissue or organ, and one or more effects of the test compound is evaluated. In a cultured or primary cell for example, the ability of the test compound to increase levels and/or activity of GBA or PS/SC can be determined. The MES cell-based models described herein can be used for such screening assays. For example, using MES cell culture plates (96- or 384-well based), small molecule-based chemical libraries are applied at a test concentration of 1 µM for a period of 36 to 48 hours. Cells are lysed and analyzed by sandwich ELISA, e.g., as outlined in FIGS. 3A to 3D herein to determine the net effect of these compounds on the alpha-synuclein protein concentration in each well.

In some embodiments, the test sample is, or is derived from (e.g., a sample taken from) an in vivo model of a synucleinopathy disorder as described herein. For example, an animal model, e.g., a rodent model such as a mouse or rat model, can be used. Specifically, the Masliah mouse model of synucleinopathy is suitable (commercially available from JSW Research in Graz, Austria) (see, Masliah et al., Science, 2000 Feb. 18; 287(5456):1265-9.

Methods for evaluating each of these effects are known in the art. For example, ability to modulate expression of a protein can be evaluated at the gene or protein level, e.g., using quantitative PCR or immunoassay methods. In some embodiments, high throughput methods, e.g., protein or gene chips as are known in the art (see, e.g., Ch. 12, Genomics, in Griffiths et al., Eds. Modern genetic Analysis, 1999, W. H. Freeman and Company; Ekins and Chu, 1999 Trends in Bio-technology, 17:217-218; MacBeath and Schreiber, 2000 Science, 289(5485):1760-1763; Simpson, Proteins and Proteomics: A Laboratory Manual, Cold Spring Harbor Laboratory Press; 2002; Hardiman, Microarrays Methods and Applications: Nuts & Bolts, DNA Press, 2003), can be used to detect an effect on two, three, four, five or more of the polypeptides described herein.

A test compound that has been screened by a method described herein and determined to increase levels and/or activity of GBA or PS/SC, or to decrease levels of aS aggregates, can be considered a candidate compound. A candidate compound that has subsequently been screened, e.g., in an in vivo model of a disorder, e.g., an animal model of a synucleinopathy disorder, and determined to have a desirable effect on the disorder, e.g., on one or more symptoms of the disorder, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified as "hits" (e.g., test compounds that increase levels and/or activity of GBA or PS/SC) in a first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating synucleinopathy disorders as described herein. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can be further screened by administration to an animal model of a synucleinopathy disorder as described herein. The animal can be monitored for a change in the disorder, e.g., for an improvement in a parameter of the disorder, e.g., a parameter related to clinical outcome.

EXAMPLES

The invention is further described in the following examples, which do not limit the scope of the invention described in the claims.

Example 1

Glycosphingolipids Biochemically Associate with α-Synuclein In Vitro

The experiment performed in this example demonstrates the existence of stable complexes between α-synuclein protein and human brain gangliosides, which ultimately become substrates of the GBA enzyme.

Gangliosides are complex glycosphingolipids, which contain a glucocerebroside unit as part of their chemical structure (see, e.g., Dreisewerd et al., (2005) Anal Chem., 77, 4098-107). As a consequence, glucocerebroside units constitute both a building block and a degradation product in the continuous synthesis-degradation cycle of gangliosides. Co-incubation of a group of well characterized, brain-derived gangliosides (see, Schlossmacher et al., (2005) N.E.J.M., 352, 728-731, and Dreisewerd et al. (2005)) with recombinant α-synuclein protein in vitro led to the formation of a complex that was stable under highly denaturing SDS/PAGE conditions, prompting an electrophoretic shift of the 16 kDa α-synuclein complex to the 19-20 kDa higher molecular weight α-synuclein protein/glucocerebroside complex as indicated by Western blotting (FIG. 1).

FIG. 1 is a representation of a Western Blot, demonstrating the time dependent formation of a stable 19-20 kDa complex (αS/G) between human brain gangliosides and α-synuclein protein in vitro. Human brain derived gangliosides (G) were co-incubated with recombinant human α-synuclein protein (αS; wild-type) at 4° C. for various periods of time up to 72 hours, before being subjected to SDS/PAGE. As a negative control (C), water was incubated with recombinant human α-synuclein protein for 72 hours. The time dependent appearance of an upper band migrating at 19-20 kDa was noted in the samples incubated with gangliosides, but not with water, and was interpreted as a stable α-synuclein protein-ganglioside (αS/G) complex. The presence of uncomplexed α-synuclein protein is indicated by a band with the molecular weight of 16 kDa.

These and related findings demonstrated that α-synuclein protein can interact with glucocerebroside-containing, complex lipids in a manner that is highly stable and relatively resistant to the presence of SDS.

Example 2

Glucocerebroside Biochemically Associates with α-Synuclein Protein In Vitro

Human tissue-derived or synthetic Glucocerebroside (aka as glucosylceramide; GC) is co-incubated with recombinant human α-synuclein protein (αS; wild-type) at 4° C. for various periods of time up to 72 hours, before being subjected to SDS/PAGE. As a negative control (C), water is incubated with recombinant human α-synuclein protein for 72 hours. The time dependent appearance of an upper band migrating at approximately 19-22 kDa should be noted in the samples incubated with glucocerebroside. The presence of uncomplexed α-synuclein protein is indicated by a band with the molecular weight of 16 kDa.

These and related findings demonstrate that α-synuclein protein can interact with glucocerebroside in a manner that is highly stable and relatively resistant to the presence of SDS.

Example 3

Glucosphingosine Biochemically Associates with α-Synuclein Protein In Vitro

Human tissue—derived or synthetic Glucosphingosine (aka as glucosylsphingosine; GS) is co-incubated with recombinant human α-synuclein protein (αS; wild-type) at 4° C. for various periods of time up to 72 hours, before being subjected to SDS/PAGE. As a negative control (C), water is incubated with recombinant human α-synuclein protein for 72 hours. The time dependent appearance of an upper band migrating at approximately 19-22 kDa should be noted in the samples incubated with glucosphingosine. The presence of uncomplexed α-synuclein protein is indicated by a band with the molecular weight of 16 kDa.

These and related findings demonstrate that α-synuclein protein can interact with glucosphingosine in a manner that is highly stable and relatively resistant to the presence of SDS.

Example 4

Establishment of a Dopamine-Expressing Neural Cell Culture System for α-Synuclein Protein Expression A dopamine-expressing rodent mesencephalic cell culture system (MES23.5 cells) was utilized for the establishment of an α-synuclein protein over-expression system. Previously, these cells had been used by Sharon et al. to create stable cells lines over-expressing αS. However, these authors observed that stable αS-transfected MES23.5 cell clones gradually loose αS expression after passaging for 2-months or more (Sharon R, et al., (2001) PNAS 98, 9110-9115). To avoid this problem, in this work, MES23.5 cells were transiently transfected each time using Lipofectamine® 2000 (Invitrogen Corp). Since the MES23.5 cells are only loosely adherent to tissue culture plastic dishes, the cells were cultured on poly-D-Lysine coated plastic dishes, a measure that was not previously used in the literature. Furthermore, Invitrogen Corp recommends transfecting with Lipofectamine 2000 when cells are >80% confluent, it was empirically found here in this study that the transfection efficiency was much improved by transfecting when cells are 50-60% confluent (as measured by transfection efficiency of a Green Fluorescent Protein (GFP)— encoding plasmid in sister wells, visualized 24 hours after transfection under a fluorescent microscope).

Figure 2A:
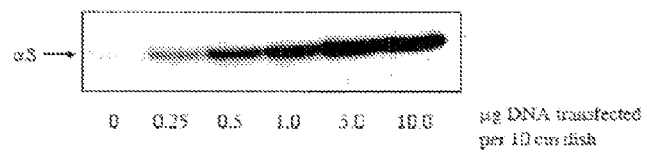
FIG. 2A is a representation of a Western Blot, of α-synuclein protein expressed in MES23.5 cells transiently transfected with indicated levels of an α-synuclein cDNA plasmid.

As shown in FIG. 2A, MES23.5 cells were transiently transfected with a full-length αS encoding SNCA cDNA—plasmid under the control of a CMV promoter. Cells were transfected with 0, 0.25, 0.5, 1, 5, and 10 μg (per 10 cm dish) of plasmid. 24 hours later, cells were washed with Tris-buffered saline and lysed in 140 mM NaCl, 50 mM Tris-Hcl, pH 8.0, 1 mM EDTA, 0.5% Triton-X100, and 1× protease inhibitors. Lysates were centrifuged at 100,000×g for 30 min at 4° C.; the top ⅔ of supernatants were removed and frozen in siliconized tubes at −80° C. Samples were run on SDS/PAGE, using 1 mM DTT as the reducing agent. Expression of the αS protein was confirmed at 24 hours post-transfection by Western blotting, where cell lysates were probed with a monoclonal antibody against αS protein (syn-1 antibody, BD Transduction Labs). Expression was shown to be dependent on the initial amount of plasmid transfected, up to a saturating amount of 5-10 μg per 10 cm dish.

Example 5

Figure 2B:
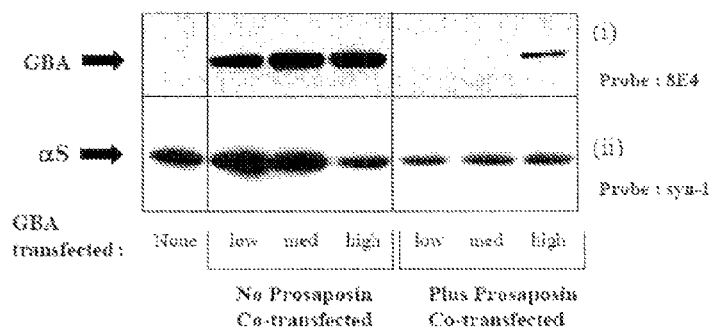
FIG. 2B is a representation of a Western Blot indicating the effects of GBA cDNA transfection, +/−prosaposin cDNA transfection on the intracellular α-synuclein protein levels in MES23.5-syn cells. The levels of the latter protein are shown in the lower panel of the Western blot.

Exploratory Studies Using of MES23.5 Cells for the Concomitantly Expression of α-Synuclein and Selected Lysosomal Proteins The experiment performed in this example (as shown in FIG. 2B) demonstrates that increased levels in cellular GBA protein can reduce the level of neural α-synuclein protein.

MES23.5 cells were transfected with 0.5 μg αS-encoding SNCA cDNA per 10 cm dish plus either 1.25, 2.5 or 5 μg (low, medium, or high) GBA-encoding cDNA in the absence or presence of 5 μg of Prosaposin-encoding cDNA. All arms of the experiment were balanced up to a total of 10.5 μg cDNA per 10 cm dish using empty vector cDNA. The GBA- and Prosaposin-encoding cDNA plasmids under a CMV promoter, as well as the pCMV-XL5 empty vector were purchased from OriGene Technologies, Inc (clones had been fully sequence-verified after isolation and a maxiprep). 24 hours later, cells were lysed and probed for GBA and αS protein levels. The upper panel in of FIG. 2B3 is a representation of a Western Blot indicating expression of GBA protein in the absence and presence of co-transfected prosaposin. GBA was probed using the monoclonal antibody 8E4. GBA over-expression occurred in a slightly gene-dosage dependent way in the absence of prosaposin. In the presence of prosaposin over-expression, the GBA signal itself was decreased. This observation can be explained by a modification of GBA during its activation, leading to its reduced recognizability by the monoclonal antibody employed under these SDS/PAGE/Western blotting conditions, by a faster intra lysosomal degradation rate of GBA after its activation by PS/SC, or it may have occurred as a result of overall reduced cDNA transcription and translation rates given the concomitant delivery of three distinct exogenous cDNA-carrying plasmids.

The lower panel of FIG. 2B shows that GBA, in the absence of co-transfected prosaposin, lowered the co-expressed α-synuclein protein levels at the largest amount of co-transfected GBA cDNA. This observed α-synuclein protein lowering effect by GBA was greatly potentiated by the co-expression of prosaposin, as indicated by the strong decrease in α-synuclein protein levels at even the lower concentrations (low and medium) of transfected GBA-encoding cDNA. The bar graph in FIG. 2C demonstrates a semi quantitative summary of the data shown in FIG. 2B.

In summary, it was concluded that increased GBA activity under these ex vivo cell culture conditions can lower α-synuclein steady-state levels, especially in the presence of elevated PS/SC. Thus, this strategy can be used to lower α-synuclein steady-state levels in vivo, including in the human brain that is at risk for—or already affected by—critically elevated levels of α-synuclein content, e.g., in a subject having a synucleinopathy disorder. Accordingly, strategies to increase GBA activity and/or PS/SC levels in vivo represents a novel avenue for neuroprotective treatment of Parkinson's Disease (PD) and related synucleinopathies.

Example 6

Establishment of a First-in-Kind, Sensitive and Precise ELISA System to Quantitatively Determine α-Synuclein Concentrations in Transfected MES23.5 Cells For further experiments and investigations, it was desired to decrease reliance on Western blot methods, which are low throughput and have limited dynamic range, and instead to create a quantitative sandwich ELISA (enzyme-linked immune-adsorbent assay) system for medium-throughput quantification of αS with improved sensitivity, optimized specificity and dynamic range.

Sera from 6 rabbits were raised and affinity-purified at Open Biosystems, Inc. (http://www.openbiosystems.com) against recombinant, full-length human αS. Recombinant αS had been HPLC- and MS-characterized and subjected to amino acid composition and protein concentration analyses. For ELISA, 384-well MaxiSorp plates (Nunc, Inc) were coated with 50 μl/well capturing polyclonal Ab (hSA-2)

diluted in coating buffer (NaHCO3 with 0.2% NaN3, pH 9.6). Following washes with PBS/0.05% Tween-20 (PBS-T), plates were blocked for 2 hours at 37° C. in blocking buffer (1.125% fish skin gelatin; PBS-T). After 4 washes, samples were loaded and incubated at 4° C. for 12 hrs. Biotinylated Syn-1 mAb (as the assaying Ab) was generated using 200 μg Sulfo-NHS-LC Biotin (Pierce), diluted in blocking buffer and added to the plate for 2 hrs at 37° C. Following 4 washes, ExtrAvidin phosphatase (Sigma) diluted in blocking buffer was applied for 1 hr at 37° C. Color development was carried out by using Fast-p-Nitrophenyl Phosphate (Sigma) and monitored kinetically at OD 405 nm every 5 min for up to 60 min.

Figure 3A:
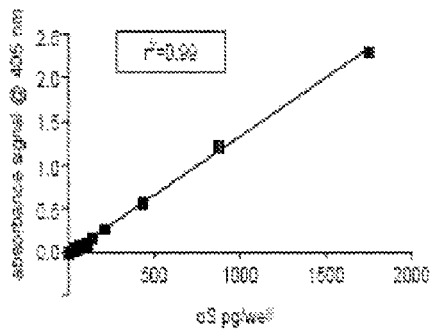
FIG. 3A is a graph of the performance of a sandwich ELISA that specifically detects increasing amounts of recombinant α-synuclein protein (x-axis), as monitored by OD absorbance reading (y-axis).
Figure 3B:
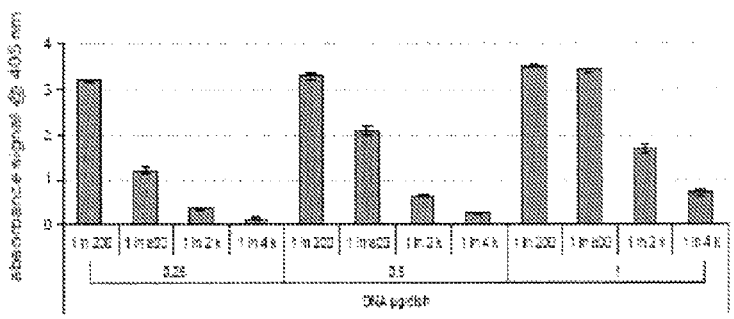
FIG. 3B is a bar graph of ELISA measurements indicating the intra-cellular α-synuclein protein levels detected in MES23.5-syn cells in the presence of increasing amounts of SNCA (synuclein, alpha (non A4 component of amyloid precursor)) cDNA (x-axis) that was transfected into these cells, where lysates were diluted in a serial manner from 1 in 200 to 1 in 4,000.

Various concentrations of highly purified, recombinant, human αS (r-haS) were used as standards to establish ELISA sensitivity and assay range, as shown in FIG. 3A ($r^2$>0.98).

To optimize a 'DNA:Lipofectamine® 2000' ratio with low cell toxicity, MES23.5 cells were transfected with either 0.25, 0.5 or 1 μg αS-encoding, wild-type, human SNCA cDNA plus empty vector cDNA up to a total of 5.5 μg DNA per 10 cm dish. 24 hours after transfection, cell lysates were harvested as described above. For serial dilutions of cell lysates, blocking buffer containing 0.5% lysate from vector-transfected wells was used as diluent, which was also used to create the blank and the corresponding standard curve of recombinant human αS. Saturation kinetics were examined for identification of time point(s) where standards and sample dilutions were in the log phase.

Figure 3C:
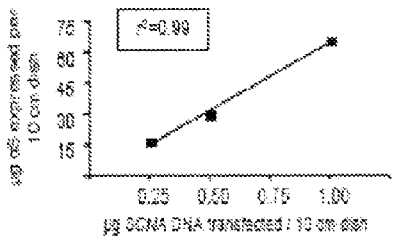
FIG. 3C is a regression analysis of the concentration of intracellular α-synuclein protein after a given amount of transfected SCNA cDNA, as measured by sandwich ELISA, and as interpolated from the data obtained in FIG. 3A and FIG. 3B.

When analyzing these cell lysates by ELISA concentrations in MES-αS cells were recorded that showed the expected parallelism after serial dilution, that were SCNA cDNA dose-dependent (both aspects are demonstrated in the graph of FIG. 3B), and that permitted for the first time the precise calculation of the total amount of αS protein concentration expressed in living cells (as shown in FIG. 3C).

Figure 3D:
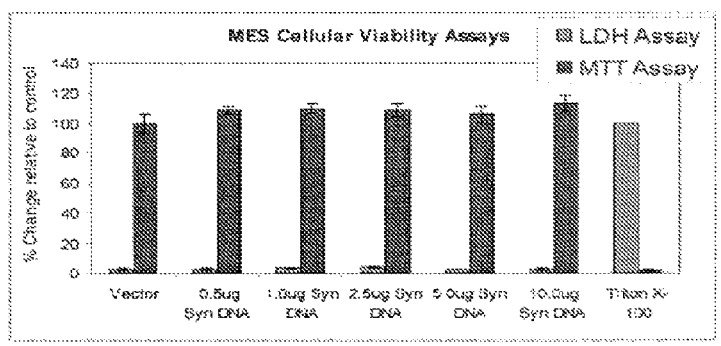
FIG. 3D is a bar graph showing the results of lactate dehydrogenase (LDH) and MTT assays confirming full cellular viability of the α-synuclein protein expressing MES-syn cells, 24 hours after transfection.

It was also confirmed that under these refined conditions of cellular expression the viability of MES23.5 and MES-syn cells was not altered, as measured by LDH in conditioned medium (lactate dehydrogenase, a normally cytosolic enzyme), as a marker of cell leakiness, and by cellular conversion of MTT ((3-(4,5-Dimethylthiazol-2-yl)-2,5-diphenyltetrazolium bromide) to formazan, as a marker of intact cellular metabolism. For these standard toxicity assays, a positive control leading to 100% cell lysis (0.1% Triton-X® 100 treatment) was performed in parallel. The results are shown in FIG. 3D. It was determined that for the range of cDNA concentrations chosen in all experiments, MES-αS and MES-vector cells were metabolically fully active in the MTT assay and showed no release of cytosol-derived LDH into the conditioned medium of transfected and untransfected cells. Thus, both assays demonstrated cellular integrity.

Example 7

Synucleinopathy Disease-Related as Well as Catalytic Site-Directed Mutations in GBA Promote the Accumulation of α-Synuclein in Dopaminergic MES Cells The optimized cell expression/ELISA read-out system described in Example 6 was used to examine the effects of over-expression of mutant GBA proteins on αS levels in MES23.5 cells.

MES cells were transfected with 0.5 μg per 10 cm dish of αS-encoding SNCA cDNA-carrying plasmid, plus 5 μg per 10 cm dish of wild-type or mutant, human GBA-encoding plasmid. The GBA variants used were wild type, N370S, D409H, L444P, E235A, and E340A. These 5 GBA mutants were created by site-directed mutagenesis, using the Quickchange® kit (Stratagene), and sequence-verified. The N370S, D409H and L444P are known to occur (in the homozygous or compound heterozygous state) in Gaucher disease in the heterozygous state in Parkinson Disease patients and/or patients with dementia with Lewy bodies. The E235A and E340A mutant GBA proteins are not known to occur in people. They are directed at the acid/base catalyst and nucleophile, respectively, of the GBA enzyme, and have previously been shown to be catalytically inactive, despite being properly trafficked to the lysosome (Fabrega et al., 2000, Glycobiology, vol 10, pp 1217-1224).

Figure 2C:
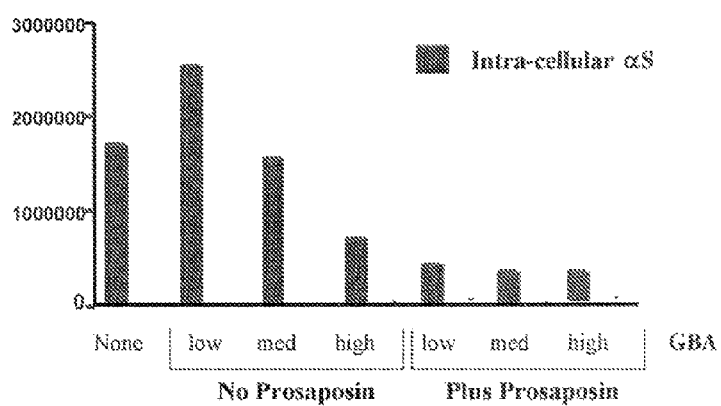
FIG. 2C is a bar graph of ELISA measurements indicating the intra-cellular α-synuclein protein levels detected in MES-syn cells in presence or absence of prosaposin and dependent on the amount of co-transfected GBA DNA.

24 hours after transfection, MES cells were lysed as described above and all lysates were analyzed by ELISA. As demonstrated in a composite bar graph that summarize several ELISA experiments (shown in FIG. 4), when comparing the changes in α-synuclein steady-state to known quantities of recombinant α-synuclein protein that was loaded in parallel, it was recorded that the co-expression (5 μg/10 cm dish) of wild-type GBA (but not prosaposin) with αS under these conditions did not significantly change αS levels (109.7+/−9.88% of vector cDNA control levels). This is in contrast to the result observed in Example 5 above. The observed discrepancy can reflect the differences in total DNA transfected in the two paradigms (FIG. 2B; FIG. 2C versus FIG. 4), thereby leading to changes in the DNA:Lipofectamine® 2000 ratio, and in the role of co-expressed prosaposin (saposin C). It is therefore conceivable that wild-type GBA can have variable effects on αS levels in these MES23.5 cells, depending on the rate of αS import into lysosomes and the composition as well as activation state of more than one lysosomal enzyme.

Figure 4:
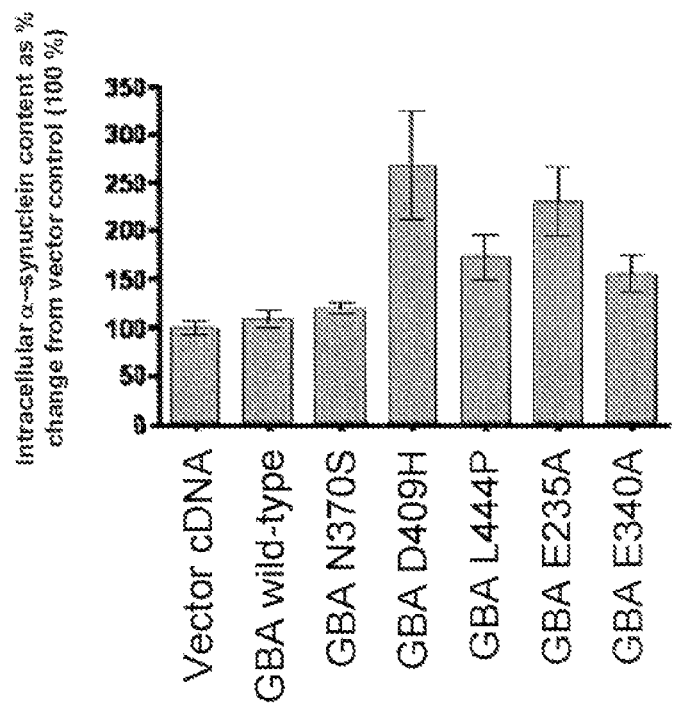
FIG. 4 is a representation of sandwich ELISA results from five separate experiments, which indicate a 20 to >270 percent rise in intracellular α-synuclein protein levels in MES23.5 cells following the expression of mutant GBA polypeptides that carry one of several missense mutations that were recently linked to Parkinson disease and dementia with Lewy bodies, or which carry mutations detrimental to the GBA active site. The α-synuclein protein level is expressed in relation to the concentration of MES-syn cells transfected with no ectopic GBA, but empty vector cDNA only.

In contrast, the co-transfection with αS of the disease-related N370S, D409H or L444P-carrying mutants of GBA (5 μg per 10 cm dish) consistently led to intracellular α-synuclein accumulation that was 121.1+/−4.98%, 269.4+/−56.6%, and 172.7+/−23.02% of control levels (mean+/−standard error of the mean, n=4 (to −6), from 5 independent experiments), as demonstrated in the bar graph of FIG. 4. These results help explain—for the first time—why people with N370S, D409H or L444P mutations are more susceptible to sporadic Parkinson's Disease. It is interesting that the mutation which generally produces the mildest form of Gaucher disease (GD), namely N370S, promoted only a mild accumulation of αS, whereas those associated with a more severe GD phenotype promoted a more prominent accumulation of intracellular αS (see for example, GBA mutant D409H in FIG. 4).

To investigate whether the pro-accumulatory effects of GBA mutations on αS concentrations were due to a trafficking defect causing a more generalized cell stress, or a loss of enzymatic function within the lysosome, we next employed two mutants which are properly trafficked to the lysosome, but exhibit total loss of enzymatic function. Co-transfection with αS of the E235A- and E340A-missense mutation-carrying variants of GBA (5 μg per 10 cm dish) led to the intracellular α-synuclein levels that were 231.0+/−37.14% and 156.4+/−19.65% of control vector DNA levels, respectively (mean+/−sem, n=4 (−6), from 5 independent experiments), as demonstrated in the bar graph shown in FIG. 4.

Based on the results of these experiments it appears that activity loss of this non-protease-type lysosomal enzyme contributes at least in part to the αS-accumulatory effect that was induced by human disease-related GBA mutants.

Example 8

Expression of Cathepsin D Consistently and Significantly Reduces α-Synuclein Protein Levels in a Dose-Dependent Manner The system described in Example 6 was used to examine the effects of a protease-type lysosomal enzyme, namely cathepsin D, on co-transfected αS levels.

Figure 6:
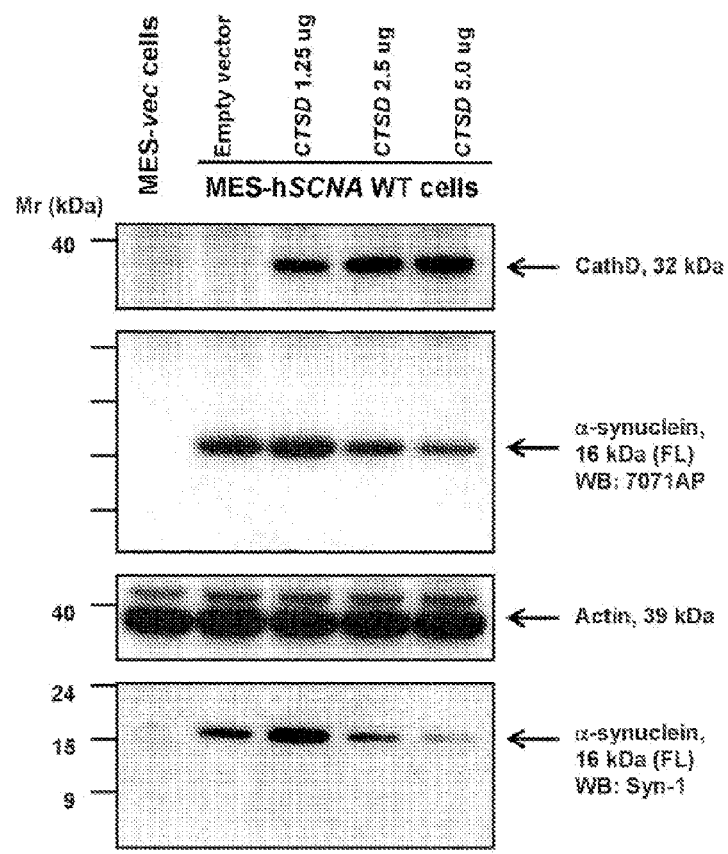
FIG. 6 is a representation of a Western Blot indicating the dose-dependent α-synuclein protein level-lowering activity of human cathepsin D when jointly expressed in MES23.5-syn cells (MES-αS).

MES23.5 cells were transfected with 0.5 μg per 10 cm dish of an αS-encoding, wild-type, human SNCA cDNA-carrying plasmid (referred to as MES-hSNCA WT cells in the Western blot shown in FIG. 6), plus either 1.25, 2.5 or 5 μg per 10 cm dish of a human Cathepsin D-encoding CTSD cDNA plasmid, which was purchased from OriGene Technologies, Inc., and was under the control of a CMV promoter. The Cathepsin D clone was fully sequence-verified after isolation and maxiprep. Each transfection arm was balanced with empty vector DNA up to a total of 5.5 μg DNA per 10 cm dish. 24 hours after transfection, cells were lysed, and the resulting lysates were analyzed by the sandwich ELISA described herein.

Figure 5:
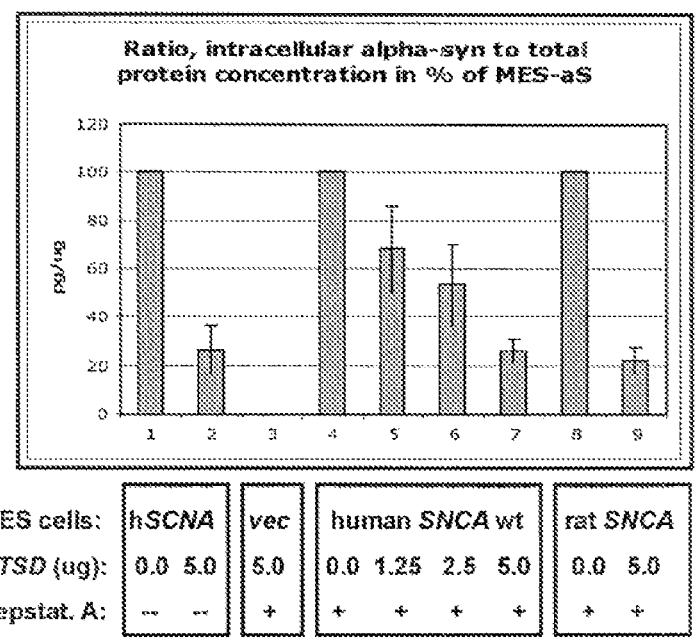
FIG. 5 is a bar graph of sandwich ELISA measurements of human and rat α-synuclein protein level-lowering activity of human cathepsin D when jointly expressed in MES23.5-syn cells (MES-αS).

As demonstrated in FIG. 5, co-expression of human cathepsin D lowered intracellular α-synuclein protein levels. This occurred in a CTSD cDNA-dosage dependent manner, in that increasing amounts of co-transfected cathepsin D resulted in a progressive lowering of intracellular α-synuclein levels. When comparing the changes in α-synuclein steady-state to known levels of recombinant α-synuclein protein that was loaded in parallel, it was calculated that the highest concentration of cathepsin D over-expression (5 μg/10 cm dish) led to an intra-cellular total α-synuclein level that was 25.3+/−7.0% of control levels (n=11, from 3 independent experiments). Lower levels of cathepsin D over-expression (1.25 μg/10 cm dish and 2.5 μg/10 cm dish) led to intracellular α-synuclein levels that were 68+/−17.7% and 53+/−16.8% of control levels, respectively (n=2, from 2 independent experiments). Similarly, human Cathepsin D was able to lower the levels of co-transfected rat αS, using the same paradigm.

To demonstrate that the αS-lowering effect of Cathepsin D indeed measured as high as 75 percent of the total amount of intracellular αS concentration detectable (and to show that the latter effect was not due to the chosen ELISA system, the results were confirmed by Western blotting. As shown in FIG. 6, cell lysates were independently probed with 2 different anti-synuclein antibodies: the monoclonal syn-1 previously described, and a rabbit polyclonal 7071AP (Periquet et al., (2007) J. Neurosci., 27:3338-46).

Importantly, the co-expression of Cathepsin D with αS for 24 hours did not lead to the generation of any visible lower or higher molecular weight species, as visualized by syn-1 and 7071AP. The same result was obtained when using a third antibody, the rabbit polyclonal, affinity-purified hSA-2 (data not shown), and when blots were over-developed during longer exposure.

To confirm that the effects of Cathepsin D took place in vivo, and not during the cell lysis procedure, the effects of a potent Cathepsin D inhibitor, pepstatin A, were examined by its presence in the cell lysis buffer. A shown in the graph bar of FIG. 5 (first two bars on the left), the inclusion of pepstatin A in the lysis buffer did not change the amount of αS detected in the lysate, thereby demonstrating that the results described in FIGS. 5 and 6 above were not an artifact of the cell lysis procedure.

To confirm that the effect of Cathepsin D on lowering of αS in MES23.5 cells was specific and was not caused by a general decrease in cellular metabolism and integrity, the MTT and LDH assays were performed on MES-syn cells that had been co-transfected with the highest amount of Cathepsin D-encoding cDNA (5 μg/10 cm dish). Lysis of cells with 0.1% Triton-X® 100 served as a positive control, representing maximal cell death. MES-syn cells co-transfected with CTSD cDNA exhibited a normal MTT signal that was not different from the control vector transfected cells (101.3+/−3.91% and 100+/−4.05%, respectively; n=6, from 2 independent experiments). Similarly, MES-syn cells co-transfected with Cathepsin D exhibited an LDH signal that was identical to that of control vector transfected cells.

To examine whether Cathepsin D could also reduce the levels of missense mutation-carrying αS proteins, MES23.5 cells were transfected with low amounts (0.5 μg/10 cm dish) of SNCA cDNA encoding either the A30P, E46K or A53T variants of α-synuclein which are linked to familial Parkinson Disease in humans, as well as a S129D and a S129A mutant. Phosphorylation of αS at the Serine 129 residue is known to be a pathological hallmark of αS aggregates in vivo (Anderson J et al., 2006, J Biol Chem, vol 281, pp 29739-29752). Mutation of a Ser residue to Asp is known in the art to mimic sustained, serine-based phosphorylation. The S129A mutant, a phosphorylation-incompetent mutant of αS, was also included for comparison.

Figure 7:
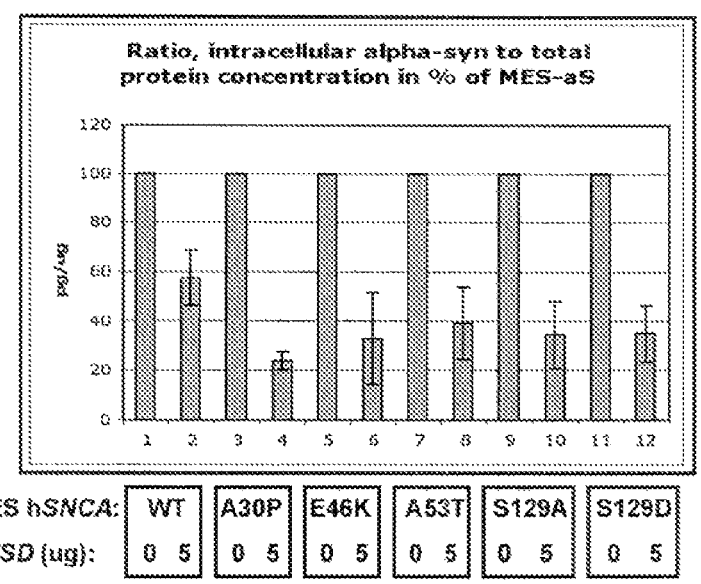
FIG. 7 is a bar graph of sandwich ELISA measurements of the human α-synuclein protein level-lowering activity of cathepsin D when jointly expressed in MES23.5-syn cells (MES-αS). Note, both wild-type α-synuclein protein can be reduced by cathepsin D as well as several mutant α-synuclein isoforms that carry missense mutations and have been previously linked to familial forms of the disease and to autopsy-confirmed Parkinson's.

As shown in the bar graph of FIG. 7, the co-expression of Cathepsin D-encoding CTSD cDNA (5 μg/10 cm dish) with either A30P, E46K, A53T, S129D, or S129A αS caused a similar degree reduction in αS levels for all αS proteins examined, when compared to their co-expression with empty vector DNA. When comparing the changes in α-synuclein steady-state to well-characterized levels of recombinant α-synuclein protein that was loaded in parallel, it was estimated that cathepsin D over-expression (at a cDNA concentration of 5 μg/10 cm dish) led to intracellular α-synuclein levels that were 23.98+/−3.57%, 33.08+/−18.51%, 39.21+/−14.63%, 34.84+/−11.36% and 34.31+/−13.39% of cognate control levels, for A30P, E46K, A53T, S129D, or S129A αS polypeptides, respectively (n=2 (−3) from 2-3 independent experiments).

This results suggest (a) that Cathepsin D is capable of also degrading the mutant forms of αS which occur in familial PD and (b) that phosphorylation or dephosphorylation at the Ser129 residue of αS does not alter the proteolytic ('synucleinase') activity exhibited by Cathepsin D towards αS.

Of note, residues D98 and Q99 of αS represent the motif by which αS is recognized by the Lamp2a receptor during chaperone mediated autophagy (CMA); Cuervo et al, 2004, Science, vol 305, pp 1292-1295). To investigate the importance of this motif in the αS-lowering action induced by cathepsin D, MES 23.5 cells were also transfected with a cDNA (0.5 μg/10 cm dish) encoding a mutant αS variant, where the D98 and Q99 residues had both been changed to Alanine (A) by site-directed mutagenesis (i.e., DQ/AA-variant of αS). When comparing the changes in the DQ/AA-αS steady-state to well-characterized levels of recombinant α-synuclein protein that was loaded in parallel, it was estimated that cathepsin D over-expression (5 μg/10 cm dish) led to intracellular DQ/AA αS levels that were 22.14+/−5.32% of the vector control levels, (n=3, from 3 independent experiments; not shown). Based on these results, it appears that either alpha-synuclein also enters the lysosome by a method other than Lamp2α-mediated CMA, or Cathepsin D exhibits and/or induces extra-lysosomal activities synucleinase activity.

Example 9

Expression of Cathepsin F Reduces α-Synuclein Protein Levels

The system described in Example 6 was used to examine the effects of another lysosomal cathepsin enzyme, namely cathepsin F, on co-transfected αS levels.

MES23.5 cells were transfected with 0.5 µg per 10 cm dish of αS-encoding SCNA cDNA plasmid, plus 5 µg per 10 cm dish of a human Cathepsin F-encoding, human CTSF plasmid, which was purchased from OriGene Technologies, Inc., and was under the control of a CMV promoter. The Cathepsin F clone was fully sequence-verified after isolation and maxiprep. 24 hours after transfection, cells were lysed and lysates were analyzed by sandwich ELISA.

Twenty-four hours post-transfection, co-expressed human cathepsin F protein lowered the intracellular α-synuclein protein concentration, as measured by sandwich ELISA. When comparing the changes in α-synuclein steady-state levels to well-characterized levels of recombinant α-synuclein protein that were loaded in parallel, it was estimated that cathepsin F over-expression (5 µg/10 cm dish) led to intracellular α-synuclein levels that were 51.7+/−14.1% of control levels (n=3, from 2 independent experiments).

To confirm that the effect of Cathepsin F on lowering of αS was specific and was not caused by a general decrease in cellular integrity, the LDH assay was performed on MES-syn cells that had been co-transfected with Cathepsin F-encoding CTSF cDNA (5 µg/10 cm dish). Lysis of cells with 0.1% Triton-X 100 served as a positive control for cell toxicity, promoting maximal cell death. MES-syn cells co-transfected with Cathepsin F exhibited an LDH signal that was less than or equal to that of control vector transfected cells (data are from 2 independent experiments; not shown).

Example 10

Increased GBA Activity Prevents Accumulation of α-Synuclein in a Mouse Model

A mouse model in which the wild-type, human α-synuclein protein is moderately overproduced in the brain can be used as a model for the accumulation of α-synuclein protein in cell bodies of the brain. GBA activity level in the central nervous system is increased either by treating the mice with isofagomine (IFG), an imino sugar that has been shown to increase GBA activity in mice and humans (Lieberman R et al., (2007) Nat Chem. Biol. February; 3(2):101-7), or a isofagomine-like substance, or by administering or over-expressing GBA protein in the mice. The increased GBA activity prevents the age-dependent accumulation of α-synuclein protein in neural cells of the central and/or peripheral nervous system.

Example 11

Increased GBA Activity Provides Therapeutic Effect in a Parkinson's Mouse Model

The therapeutic effect of increasing GBA activity in neurons is confirmed in a novel familial Parkinson's disease model, C3H-Tg (SNCA)83Vle, by showing decreased accumulation of α-synuclein aggregates in the brain of the test animals. This mouse model expresses mutant A53T human α-synuclein under the control of mouse prion (prnp) protein promoter. The prnp promoter has been shown to accomplish high levels of gene expression in most neurons of the central nervous system. By 8 months of age, homozygous B6; C3H-Tg(SNCA)83Vle mice begin to develop progressive phenotype and age-dependent intracytoplasmic neuronal inclusions, similar to those seen in patients affected with synucleinopathies. Increased GBA activity prevents the age-dependent accumulation of α-synuclein in cell bodies of the brain and reduces the disease phenotype.

Example 12

Increased Cathepsin D Activity Prevents Accumulation of α-Synuclein in a Mouse Model A mouse model in which the wild-type or mutant human α-synuclein protein is moderately overproduced in the brain can be used as a model for the accumulation of α-synuclein protein in cell bodies of the human brain. Cathepsin D activity is increased either by treating the mice systemically or by infusion of the brain or stereotactically with a small molecule activator or stabilizer of Cathepsin D activity, or by administering or overexpressing Cathepsin D protein or its pre-pro-protein in vivo. The increased Cathepsin D activity prevents the age-dependent accumulation of α-synuclein protein in cell bodies of the brain. Of course, the same tests can be conducted using other cathepsin polypeptides, prepolypeptides, and with polynucleotides encoding the same.

Example 13

Increased Cathepsin D Activity Provides Therapeutic Effect in a Parkinson's Mouse Model The therapeutic effect of increasing Cathepsin D activity in neurons is confirmed in a novel familial Parkinson's disease model, C3H-Tg (SNCA)83Vle by showing decreased accumulation of α-synuclein aggregates in the brain of the test animals. This mouse model expresses mutant A53T human α-synuclein under the control of mouse prion (prnp) protein promoter. The prnp promoter has been shown to accomplish high levels of gene expression in most neurons of the central nervous system. By 8 months of age, homozygous B6; C3H-Tg(SNCA)83Vle mice begin to develop progressive phenotype and age-dependent intracytoplasmic neuronal inclusions, similar to those seen in patients affected with alpha-synucleinopathies. Increased Cathepsin D activity prevents the age-dependent accumulation of α-synuclein in cell bodies of the brain and reduces the disease phenotype. Of course, this model can be used to test other cathepsins in a similar manner.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating a subject with a synucleinopathy, but not a clinically diagnosed lysosomal storage disease, the method comprising administering to a subject an acid-beta-glucocerebrosidase (GBA) polypeptide or a polynucleotide encoding an acid-beta-glucocerebrosidase (GBA) polypeptide in an amount effective to reduce a level of α-synuclein in the subject's nervous system or in the subject's lysosomal compartment.

2. The method of claim 1, wherein the synucleinopathy is a primary synucleinopathy.

3. The method of claim 2, wherein the synucleinopathy comprises any one or more of: Parkinson's disease (PD); sporadic or heritable dementia with Lewy bodies (DLB); pure autonomic failure (PAF) with α-synuclein deposition; multiple system atrophy (MSA); hereditary neurodegeneration with brain iron accumulation; and incidental Lewy body disease of advanced age.

4. The method of claim 1, wherein the synucleinopathy is a secondary synucleinopathy.

5. The method of claim 4, wherein the synucleinopathy comprises any one or more of: Alzheimer's disease of the Lewy body variant; Down's syndrome; progressive supranuclear palsy; essential tremor with Lewy bodies; familial parkinsonism with or without dementia; tau gene and progranulin gene-linked dementia with or without parkinsonism; Creutzfeldt Jakob disease; bovine spongiform encephalopathy; secondary Parkinson disease; parkinsonism resulting from neurotoxin exposure; drug-induced parkinsonism with α-synuclein deposition; sporadic or heritable spinocerebellar ataxia; amyotrophic lateral sclerosis (ALS); and idiopathic rapid eye movement sleep behavior disorder.

6. The method of claim 1, further comprising administering one or more agents that enhance autophagy of α-synuclein complexes or enhance degradation of α-synuclein complexes within lysosomes.

7. The method of claim 6, wherein the agent comprises an mTOR inhibitor.

8. The method of claim 6, wherein the agent comprises rapamycin or a rapamycin analog.

9. The method of claim 6, wherein the agent comprises one or more of everolimus, cyclosporine, FK506, hsc70, N-octyl-4-epi-β-valienamine, and glycerol.

10. The method of claim 6, wherein the agent comprises a small molecule, a large molecule, a peptide, an antibody, a nucleic acid, or a biologically active fragment thereof.

11. The method of claim 1, wherein the subject's nervous system comprises the subject's central or peripheral nervous system, or both.

* * * * *

UNITED STATES PATENT AND TRADEMARK OFFICE
CERTIFICATE OF CORRECTION

PATENT NO. : 8,454,954 B2
APPLICATION NO. : 12/600141
DATED : June 4, 2013
INVENTOR(S) : Michael Schlossmacher et al.

It is certified that error appears in the above-identified patent and that said Letters Patent is hereby corrected as shown below:

On the Title page, column 2 under item (56), (Other Publications), line 11, delete ""Agregated" and insert -- "Aggregated --

On Title page 2, column 1 under item (56), (Other Publications), line 1, delete "Prelimianry" and insert -- Preliminary --

In the Specification

In column 1, after line 8, insert:

-- FEDERALLY SPONSORED RESEARCH OR DEVELOPMENT

This invention was made with U.S. Government support under Grant Nos. NS038375 and NS002127 awarded by the National Institutes of Health. The Government has certain rights in this invention. --

Signed and Sealed this
Third Day of September, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,454,954 B2 | Page 1 of 1 |
| APPLICATION NO. | : 12/600141 | |
| DATED | : June 4, 2013 | |
| INVENTOR(S) | : Schlossmacher et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 624 days.

Signed and Sealed this
Thirtieth Day of December, 2014

Michelle K. Lee
*Deputy Director of the United States Patent and Trademark Office*